US010030264B2

(12) United States Patent
Fedorov et al.

(10) Patent No.: US 10,030,264 B2
(45) Date of Patent: Jul. 24, 2018

(54) METHODS AND COMPOSITIONS FOR PERFORMING ANALYTICAL OPERATIONS

(71) Applicant: Pacific Biosciences of California, Inc., Menlo Park, CA (US)

(72) Inventors: Andrei Fedorov, San Bruno, CA (US); Stephen Yue, Eugene, OR (US); Lei Sun, San Jose, CA (US); Gene Shen, Santa Clara, CA (US); John Lyle, Fremont, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 571 days.

(21) Appl. No.: 14/590,650

(22) Filed: Jan. 6, 2015

(65) Prior Publication Data

US 2015/0125854 A1 May 7, 2015

Related U.S. Application Data

(63) Continuation of application No. 13/909,797, filed on Jun. 4, 2013, now Pat. No. 8,956,816.

(60) Provisional application No. 61/655,833, filed on Jun. 5, 2012.

(51) Int. Cl.
*C12Q 1/6869* (2018.01)
*G01N 33/543* (2006.01)

(52) U.S. Cl.
CPC ..... *C12Q 1/6869* (2013.01); *G01N 33/54393* (2013.01)

(58) Field of Classification Search
None
See application file for complete search history.

(56) References Cited

U.S. PATENT DOCUMENTS

| | | | |
|---|---|---|---|
| 6,056,661 A | 5/2000 | Schmidt | |
| 6,242,235 B1 | 6/2001 | Shultz | |
| 6,391,862 B1 | 5/2002 | Vigh | |
| 6,399,335 B1 | 6/2002 | Kao et al. | |
| 7,033,764 B2 | 4/2006 | Korlach et al. | |
| 7,052,847 B2 | 5/2006 | Korlach et al. | |
| 7,056,661 B2 | 6/2006 | Korlach et al. | |
| 7,056,676 B2 | 6/2006 | Korlach et al. | |
| 7,361,466 B2 | 4/2008 | Korlach et al. | |
| 7,405,281 B2 | 7/2008 | Xu et al. | |
| 7,416,844 B2 | 8/2008 | Korlach et al. | |
| 7,767,394 B2 | 8/2010 | Turner et al. | |
| 7,993,895 B2 | 8/2011 | Eid et al. | |
| 7,998,717 B2 | 8/2011 | Eid et al. | |
| 8,124,359 B2 | 2/2012 | Levison | |
| 8,252,911 B2 | 8/2012 | Bjornson | |
| 8,388,982 B2 | 3/2013 | Kong | |
| 8,404,464 B2 | 3/2013 | Ward | |
| 8,435,775 B2 | 5/2013 | Holliger | |
| 8,501,922 B2 | 8/2013 | Otto et al. | |
| 2007/0128133 A1 | 6/2007 | Eid et al. | |
| 2008/0176769 A1 | 7/2008 | Rank et al. | |
| 2009/0208961 A1 | 8/2009 | Bjornson et al. | |
| 2009/0325260 A1 | 12/2009 | Otto et al. | |
| 2010/0035269 A1 | 2/2010 | Ma | |
| 2010/0035767 A1 | 2/2010 | Holliger et al. | |
| 2010/0047802 A1 | 2/2010 | Bjorson et al. | |
| 2010/0099150 A1 | 4/2010 | Fang | |
| 2010/0159528 A1 | 6/2010 | Liu | |
| 2010/0167299 A1 | 7/2010 | Korlach | |
| 2011/0312035 A1 | 12/2011 | Ward et al. | |
| 2012/0009567 A1 | 1/2012 | Fedorov | |
| 2012/0052488 A1 | 3/2012 | Yue | |
| 2012/0142070 A1* | 6/2012 | Battrell | C12N 9/96 435/188 |

FOREIGN PATENT DOCUMENTS

| | | |
|---|---|---|
| WO | WO 2009/102470 | 8/2009 |
| WO | WO 2009/114182 | 9/2009 |
| WO | WO 2010/144150 | 12/2010 |
| WO | WO 2011/112260 | 9/2011 |

OTHER PUBLICATIONS

Eid J et al. Supporting Online Material for Real-Time DNA Sequencing from Single Polymerase Molecules. 2009. Science. p. 1-21.*
Baynes, et al., "Role of Arginine in the Stabilization of Proteins against Aggregation,"Biochemistry, v. 44, p. 4919-4925, (2005).
Chakrabarti, et al., "The Enhancement of PCR Amplification by Low Molecular Weight Amides," Nucleic Acids Research, v. 29, No. 11, p. 2377-2381 (2001).
Eckert et al., "DNA Polymerase Fidelity and the Polymerase Chain Reaction," PCR Methods Appl. 1(1): 17-24. (1991).
Eid. J., "Real-Time DNA Sequencing from Single Polymerase Molecules," Science, vol. 323, p. 133-138, (2009).
Garcia et al, "Comparison of Surfactants for Dynamic Surface Modification of Poly(Dimethylsiloxane) Microchips," Electrophoresis 26(3):703-709 (2005).
Golovanov et al., "A Smple Method for Improving Protein Solubility and Long-Term Stability," JACS 126:8933-8939 (2004).
Levene et al., "Zero-Mode Waveguides for Single-Molecule Analysis at High Concentrations" Science v. 299 n. 5607, p. 682-686 (2003).
Metzker, "Sequencing Technologies—The Next Generation," Nature Reviews Genetics, v. 11, p. 31-46 (2010).
Takashima, et al., "Artificial Molecular Clamp: A Novel Device for Synthetic Polymerases," Angew. Chem. Int. Ed. (2011), v. 50, p. 7524-7528.
Zhou et al., "One-Step Surface Modification of Poly(dimethylsiloxane) by Undecylenic Acid," Proc. of SPIE, v.7267, 726719. (2008).

* cited by examiner

*Primary Examiner* — Paul J Holland
(74) *Attorney, Agent, or Firm* — Morgan, Lewis & Bockius LLP

(57) ABSTRACT

Methods for performing analytical reactions and compositions for use in such methods, where the methods have reduced signal levels deriving from non-specific adsorption of detected reagents to other components of the analytical method, e.g., other reagents, solid phase components, vessels, etc.

17 Claims, 21 Drawing Sheets

FIG. 16
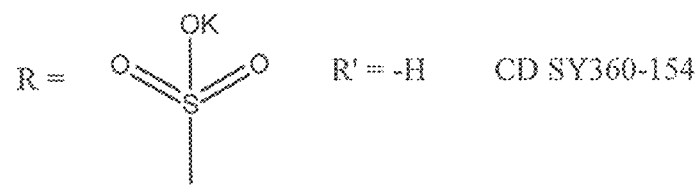# R' = -H    CD SY360-154
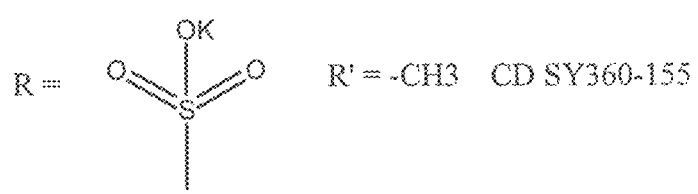# R' = -CH3   CD SY360-155
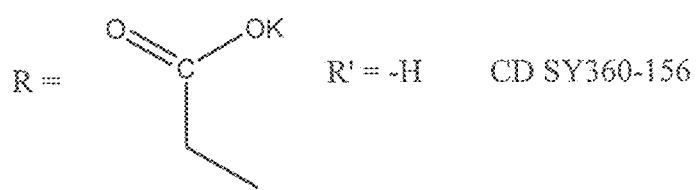# R' = -H    CD SY360-156
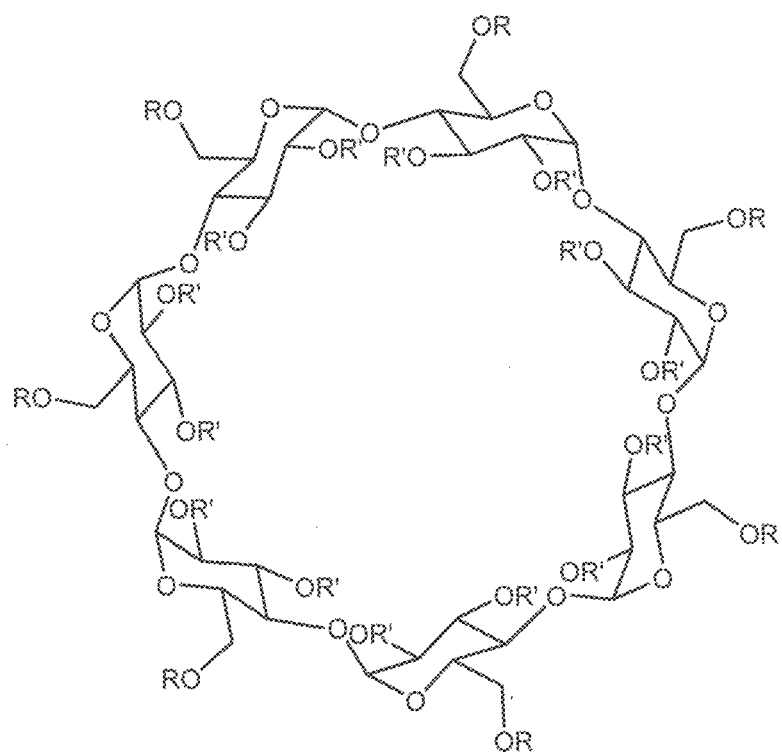

METHODS AND COMPOSITIONS FOR PERFORMING ANALYTICAL OPERATIONS

CROSS-REFERENCE TO RELATED APPLICATIONS

This application is a continuation of U.S. Ser. No. 13/909,797, filed Jun. 4, 2013, (patented on Feb. 17, 2015 as U.S. Pat. No. 8,956,816), which claims the benefit of priority to U.S. Ser. No. 61/655,833, filed Jun. 5, 2012, which are herein incorporated by reference in their entireties for all purposes.

STATEMENT REGARDING FEDERALLY SPONSORED RESEARCH

Not Applicable.

BACKGROUND OF THE INVENTION

In performing analytical reactions, e.g., analyzing chemical, biochemical, biological or other reactions, a common difficulty is maximizing the signal to noise ratio, or the ratio of relevant detected events from irrelevant or less relevant detected events that are indistinguishable from or otherwise interfere with the relevant detected events. The less relevant detected events may derive from a variety of sources, including, e.g., ambient concentrations of reactants, built up detectable products, interfering signals from other unrelated components of the analysis, e.g., solution contents, reaction vessel interference, and even instrument originating background signal levels. One major source of noise in many analytical reactions comes from the non-specific association of signal producing reaction components with components of the reaction of interest. This includes, for example, association of labeled reaction components, products etc., with solid phase components of an analytical reaction, e.g., beads, surfaces, or the like, as well as association with other reaction components, e.g., enzymes or other proteins, nucleic acids, cells, or the like.

In addition to reduction of background noise, enzymatic reactions suffer from aberrant enzyme behavior, e.g., changes in catalytic rate, pausing, dissociating, premature termination, changes in error profile, reduced rates of substrate binding and/or translocation, and the like. For example, in polymerase-mediated sequencing-by-synthesis reactions, polymerases have been observed to pause for extended periods of time before resuming normal nucleotide incorporation. In some instances, polymerase kinetics change depending on the type of nucleotide analog being incorporated. For example, some nucleotide analogs are incorporated at a slower rate than other nucleotide analogs, or the incorporation rate is highly variable during the course of a reaction. These behaviors have also been associated with shortened readlength and a worsening of other measures of sequencing performance, e.g., error metrics and overall accuracy. As such, preventing or reducing aberrant enzyme behavior in enzyme-catalyzed analytical reactions would be beneficial, e.g., to enhance enzyme performance and improve data generation.

Accordingly, it is desirable to reduce the overall level of background noise in analytical reactions, and particularly to reduce such background that derives from non-specific association of detectable reaction components with other components of the analysis. It is also desirable to increase or enhance the fluorescence intensity and/or improve fluorophore photostability. Yet further, it is desirable to prevent or reduce aberrant enzyme behavior, e.g., in order to increase readlength and accuracy of analytical reactions such as polymerase-mediated single molecule sequencing. The present invention provides solutions to these and other problems.

BRIEF SUMMARY OF THE INVENTION

The present invention is generally directed to methods and compositions for performing single molecule analytical reactions in the presence of additives.

In one aspect, the present invention provides a method of conducting an analytical reaction, where that method includes the steps of providing a reaction mixture comprising a first reaction component coupled to a surface of a solid support and a second reaction component having a detectable property and conducting the analytical reaction in the presence of at least one additive.

In a further embodiment and in accordance with the above, the present invention includes compositions for use in methods of conducting analytical reactions comprising at least one additive selected from: cholesterol, cholic acid, an amino acid, an organic solvent, and a compound comprising an aromatic ring and two —$NR_2$ substituents.

In an exemplary embodiment and in accordance with any of the above, the present invention includes compositions comprising taurocholic acid as an additive.

In an exemplary embodiment and in accordance with any of the above, the present invention includes compositions comprising a sulfonated taurocholic acid derivative as an additive.

In an exemplary embodiment and in accordance with any of the above, the present invention includes compositions comprising arginine as an additive.

In an exemplary embodiment and in accordance with any of the above, the present invention includes compositions comprising dimethylformamide (DMF) as an additive.

In an exemplary embodiment and in accordance with any of the above, the present invention includes compositions comprising dimethylacetamide (DMA) as an additive.

In an exemplary embodiment and in accordance with any of the above, the present invention includes compositions comprising N-methyl-2-pyrrolidone (NMP) as an additive.

In an exemplary embodiment and in accordance with any of the above, the present invention includes compositions comprising N,N-dimethyl-m-phenylenediamine (DMMP) as an additive.

In an exemplary embodiment and in accordance with any of the above, the present invention includes compositions comprising N,N-dimethyl-m-phenylenediamine (DMPP) as an additive.

In an exemplary embodiment and in accordance with any of the above, the present invention includes compositions comprising N-formylmorpholine (FMP) as an additive.

In an exemplary embodiment and in accordance with any of the above, the present invention includes compositions comprising an additive that is a sulfated cyclodextrin In an exemplary embodiment and in accordance with any of the above, the present invention includes methods in which the first reaction components is provided disposed on the solid support as a single molecule or single molecular complex that is resolvable from other first reaction component molecules or molecular complexes on the solid support.

In an exemplary embodiment and in accordance with any of the above, the present invention includes methods in which the solid support comprises a silica based substrate.

In an exemplary embodiment and in accordance with any of the above, the present invention includes methods in which the solid support comprises a charged surface, and the additive comprises charged groups that are oppositely charged to the charged surface.

In an exemplary embodiment and in accordance with any of the above, the present invention includes methods in which the solid support comprises a hydrophobic surface and the additive comprises a hydrophobic group.

In an exemplary embodiment and in accordance with any of the above, the present invention includes methods in which the solid support comprises a hydrophilic surface, and said additive comprises hydrophilic groups.

In an exemplary embodiment and in accordance with any of the above, the present invention includes methods in which the second reaction component comprises a fluorescent labeling moiety.

In a further embodiment, the present invention includes compositions comprising as additives substituted cyclodextrin compositions, which compositions improve the overall functioning of those analytical systems. In particular, the methods of the invention relate to single molecule analytical reactions such as sequencing and related reactions using such substituted cyclodextrin compositions. Also provided are novel substituted cyclodextrin compositions for use in such methods and in other applications.

In an exemplary embodiment, the methods of the invention include analyzing a reaction. These methods comprise providing a reaction mixture comprising a first reaction component coupled to a surface of a solid support and a second reaction component having a detectable property in the presence of a sulfated cyclodextrin having the structure:

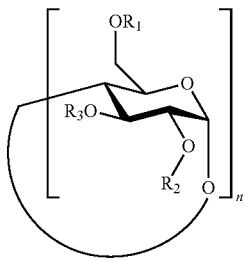

where n is from 6 to 12; $R_1$ is a group that is non-attractive to the second reaction component; $R_2$ and $R_3$ are associative groups to the surface of the solid support; and the sulfated cyclodextrin is present at an isomeric purity of at least 80%. An interaction is detected between the first reaction component and the second reaction component by detecting the detectable property of the second reaction component associated with the first reaction component.

In one embodiments, the invention provides novel compositions, such as cyclodextrin compositions, comprising the formula:

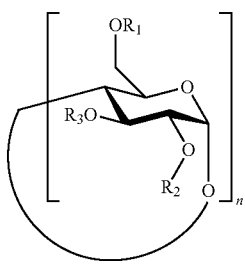

where n is from 6 to 12; $R_1$ comprises a negatively charged group; $R_2$ and $R_3$ are selected from CH2-acyl, diethylacetamide, dipropylacetamide, morpholino, piperazine, piperidine, pyrrolidine, and oxazolidine; and the sulfated cyclodextrin is present at an isomeric purity of at least 80%.

BRIEF DESCRIPTION OF THE DRAWINGS

FIG. 16 illustrates exemplary compounds of use in compositions of the present invention.

DETAILED DESCRIPTION OF THE INVENTION

Figure 1:
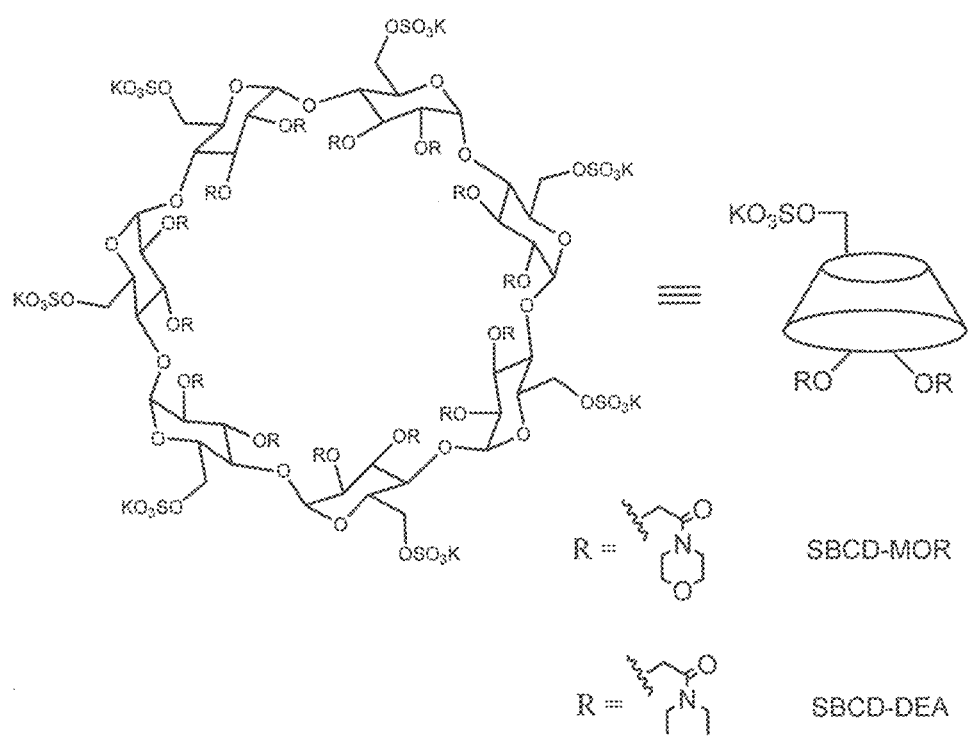
FIG. 1 shows exemplary cyclodextrin compounds according to the present invention

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, phage display, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

Note that as used herein and in the appended claims, the singular forms "a," "an," and "the" include plural referents unless the context clearly dictates otherwise. Thus, for example, reference to "a polymerase" refers to one agent or mixtures of such agents, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, compositions, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". The term "about" also includes the exact value "X" in addition to minor increments of "X" such as "X+0.1" or "X−0.1." It also is to be understood, although not always explicitly stated, that the reagents described herein are merely exemplary and that equivalents of such are known in the art.

Overview

The present invention includes both methods for performing analytical reactions and compositions for use in such methods, where the methods have reduced background signal levels deriving from non-specific adsorption of detected reagents to other components of the analytical method, e.g., other reagents, solid phase components, vessels, etc. The methods may in addition or in the alternative also result in a reduction in aberrant enzyme behavior, e.g., lower or variable enzyme activity (e.g., reduced catalytic rates, less efficient substrate binding, slower incorporation and/or translocation rates, or altered error profiles (e.g., more or different types of errors)), polymerase pausing (i.e., extended halting of incorporation of nucleotides into a nascent nucleotide strand by a polymerase), or other changes in the kinetics of catalytic activity. For example, interpulse duration (IPD) is one measure of enzyme activity that can be positively affected by addition of one or more of the additives described herein. Generally speaking and in certain embodiments, IPD is the period of time following incorporation of a nucleotide (e.g., and exit of a label from the reaction site) and prior to binding of a subsequently incorporated nucleotide in a sequencing-by-synthesis reaction.

In certain embodiments, the compositions of the present invention include additives that are able to reduce non-specific adsorption of reagents to other components of the analytical methods, including without limitation cyclodextrin, FMP, and derivatives thereof. Such compositions are further described herein and some of which are also provided in U.S. Pat. No. 8,124,359; Zhou, et al. (2008) Proc. of SPIE 7267:726719(1-10); and Garcia, et al. (2005) Electrophoresis 26(3):703-709, all of which are incorporated herein by reference in their entireties for all purposes.

In further embodiments, additives of use in methods and compositions of the invention include one or more moieties, including lipophilic moieties, that are able to provide an anchor to a surface (including without limitation a glass surface). Such additives in further embodiments also include a water solubilizing group (including without limitation a sulfonyl).

In certain exemplary embodiments and in accordance with any of the above, additives of the invention include cholesterol and compounds with similar structures to cholesterol, such as cholic acid and derivatives thereof.

In further exemplary embodiments and in accordance with any of the above, additives of the invention include organic solvents, surfactants, and/or polymer additives, including without limitation dimethylformamide ("DMF"), polyethylene glycol, and derivatives thereof. Other such additives are provided in U.S. Pat. No. 6,242,235, which is incorporated herein by reference in its entirety for all purposes.

In further aspects of the invention, additives include molecules that reduce aberrant polymerase activity, including but not limited to low or variable catalytic rates (e.g., rates of incorporation and/or translocation), changes in error profile, reduced substrate binding, and/or "pausing" during single molecule real-time sequencing, including SMRT® sequencing (described in, e.g., U.S. Pat. Nos. 6,399,335, 6,056,661, 7,052,847, 7,033,764, 7,056,676, 7,361,466, 7,416,844, the full disclosures of which are incorporated herein by reference in their entirety for all purposes and in particular for all teachings related to single molecule sequencing methods). Polymerase pausing can limit read-length in sequencing methods, because the polymerase will go through periods of quiescence/non-functioning during which normal nucleotide incorporation is paused. Typically, such polymerase pausing in a polymerization reaction represents a cessation of polymerase activity that is at least 10-, 20-, 30-, 40-, 50-, 60-, 70-, 80-, 90-, or 100-fold longer than the average IPD. Other types of aberrant polymerase activity include changes to catalytic or enzymatic rates (e.g., substrate binding, substrate incorporation, and/or translocation rates), error profile, processivity, and the like. As will be appreciated, any of the additives described herein as reducing non-specific absorption and/or binding of reactants may also serve to reduce aberrant polymerase activity, and vice versa.

In certain exemplary embodiments and in accordance with any of the above, additives that reduce polymerase pausing include without limitation amino acids (including charged amino acids such as arginine and glutamate), additives comprising an aromatic ring and two —NR2 substituents, and organic solvents. In other embodiments, such additives include DMMP, DMPP, and FMP or other morpholine derivatives.

In other exemplary embodiments and in accordance with any of the above, additives that mitigate aberrant polymerase activity include without limitation cholesterol and compounds with similar structures to cholesterol (e.g., cholic acid, taurocholic acid, etc.), poly dT oligonucleotides, and cyclodextrin derivatives (e.g., heptasulfonated cyclodextrin). For example, in reactions that include polymerase-mediated nascent strand synthesis using nucleotide analogs comprising bulky groups (e.g., a detectable label such as one or more fluorescent dye molecules attached to the nucleotide), the polymerase has a tendency to slow down such that the time between incorporation events ("interpulse duration" or IPD) is lengthened relative to the same reaction using less bulky nucleotide analogs. The increase in IPD can result in a decrease in overall read length. Addition of one or more of these additives reduces the IPD and increases the overall read length in the presence of such bulky nucleotide analogs. In certain preferred embodiments, such bulky nucleotide analogs comprise FRET labels, e.g., linked to a phosphate group that is removed during incorporation of the nucleotide monophosphate into a nascent strand by the polymerase. In other embodiments, addition of these additives not only decreases average IPD, but also reduces IPD variability, e.g., between different reactions. In yet further embodiments, possibly due to the effects on IPD, reaction rates are increase in the presence of these additives. For example, cholic acid and derivatives thereof increase overall polymerase rate in polymerization reactions. Other such additives are also provided in U.S. Patent Publication No. 2010/0035767 and Golovanov, et al. (2004) JACS 126:8933-8939, which are incorporated herein by reference in their entireties for all purposes.

In accordance with any of the above, methods of the invention utilize compositions comprising one or more additives described herein in concentrations of about 0.01-200, 0.1-190. 1.0-180, 5-170, 10-160, 15-150, 20-140, 25-130, 30-120, 35-110, 40-100, 45-90, 50-80, 55-70, and 60-65 mM. In other embodiments, methods of the invention utilize compositions comprising one or more additives described herein in concentrations of about 0.01-200, 0.1-190. 1.0-180, 5-170, 10-160, 15-150, 20-140, 25-130, 30-120, 35-110, 40-100, 45-90, 50-80, 55-70, and 60-65 µM.

Although the following sections disclose exemplary additives of use in the present invention separately, the current invention also encompasses any combination of the additives disclosed herein as well as those known in the art.

Cholesterol and Similar Compounds

As discussed above, one characteristic of some embodiments of additives of use in the present invention are that these additives include a moiety that is able to provide an anchor to surfaces. These additives may in further embodiments also carry a water solubilizing group. Exemplary embodiments of additives with these characteristics include cholesterol and compounds with similar skeletons to cholesterol, such as cholic acid. Such additives can include a liphophilic moiety that serves as an anchor to surfaces (including glass surfaces or exposed areas of coated glass surfaces). Such additives can also include a water solubilizing group.

Figure 6:
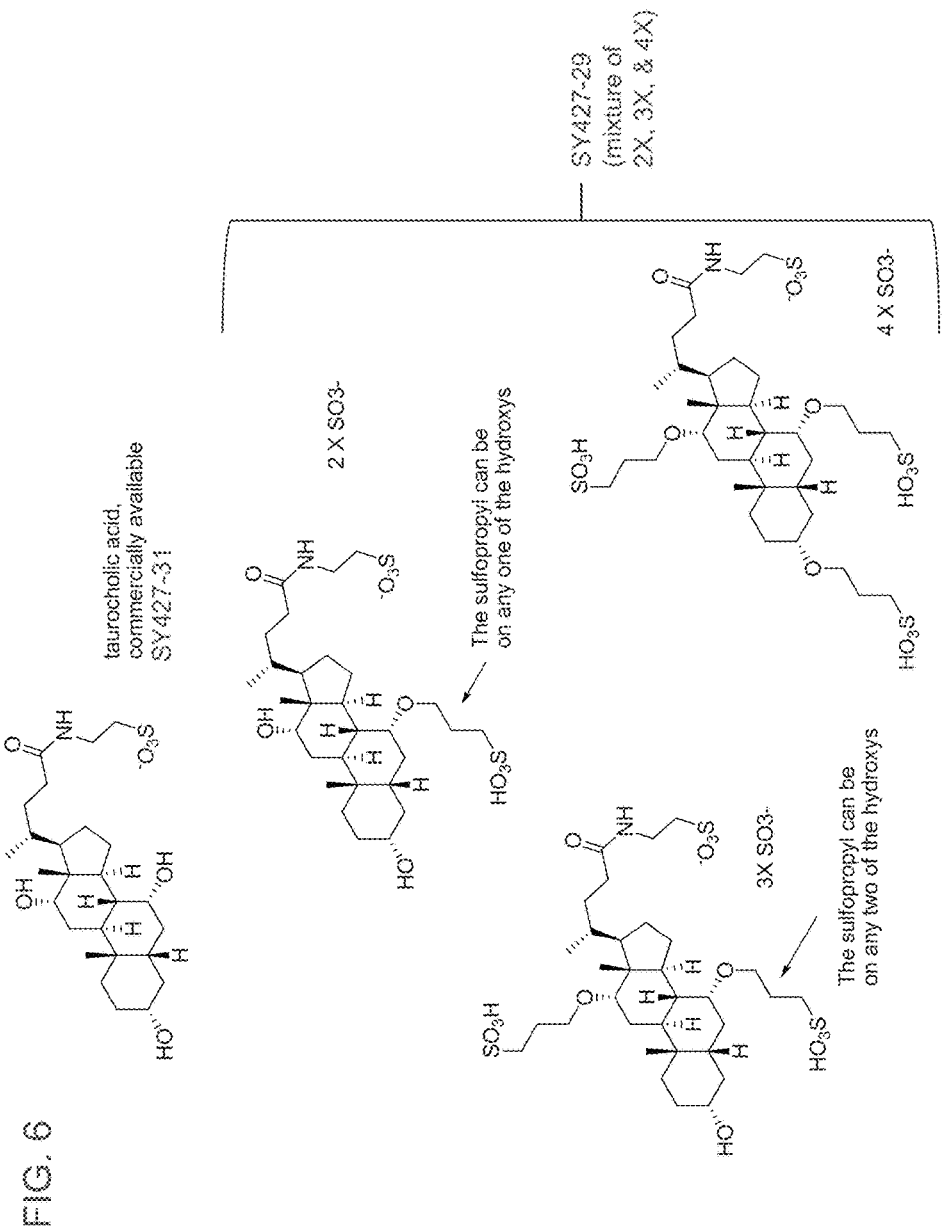
FIG. 6 illustrates exemplary compounds of use in compositions of the present invention.
Figure 21:
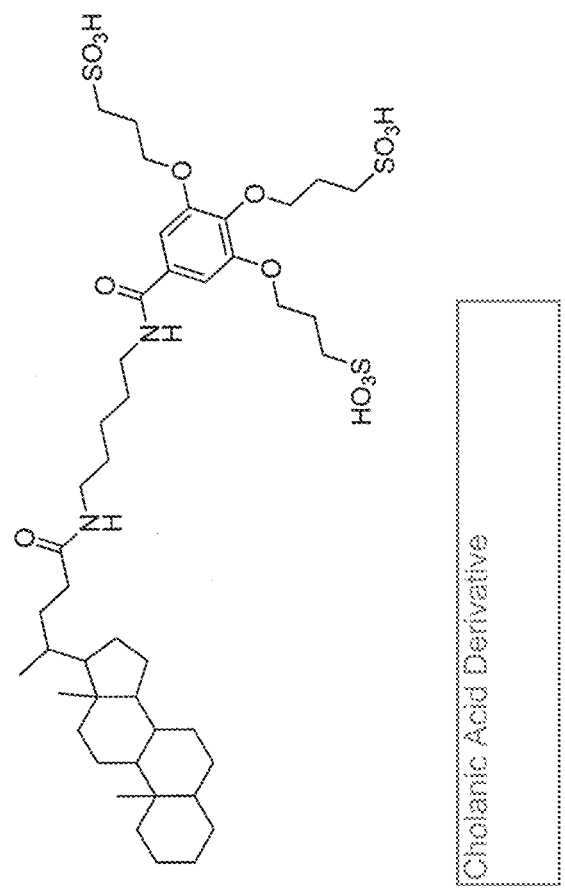
FIG. 21 shows an exemplary compound for use in compositions in the present invention.

In a specific embodiment, cholic acid with a water soluble subunit is used as an additive in methods and compositions of the invention. In a further embodiment, sulfonic cholic acid derivatives are used. In a still further embodiment, sulfonated cholic acid derivatives of use in the present invention include without limitation the compounds illustrated in FIGS. 6 and 21. As is also depicted in FIG. 6, the sulfopropyl moiety can be attached to any of the hydroxy moieties in the cholic acid derivatives of use in the present invention. In yet further embodiments, taurocholic acid is used as an additive in compositions of the present invention. In a further embodiment, the taurocholic acid used is in a potassium salt form.

Figure 18:
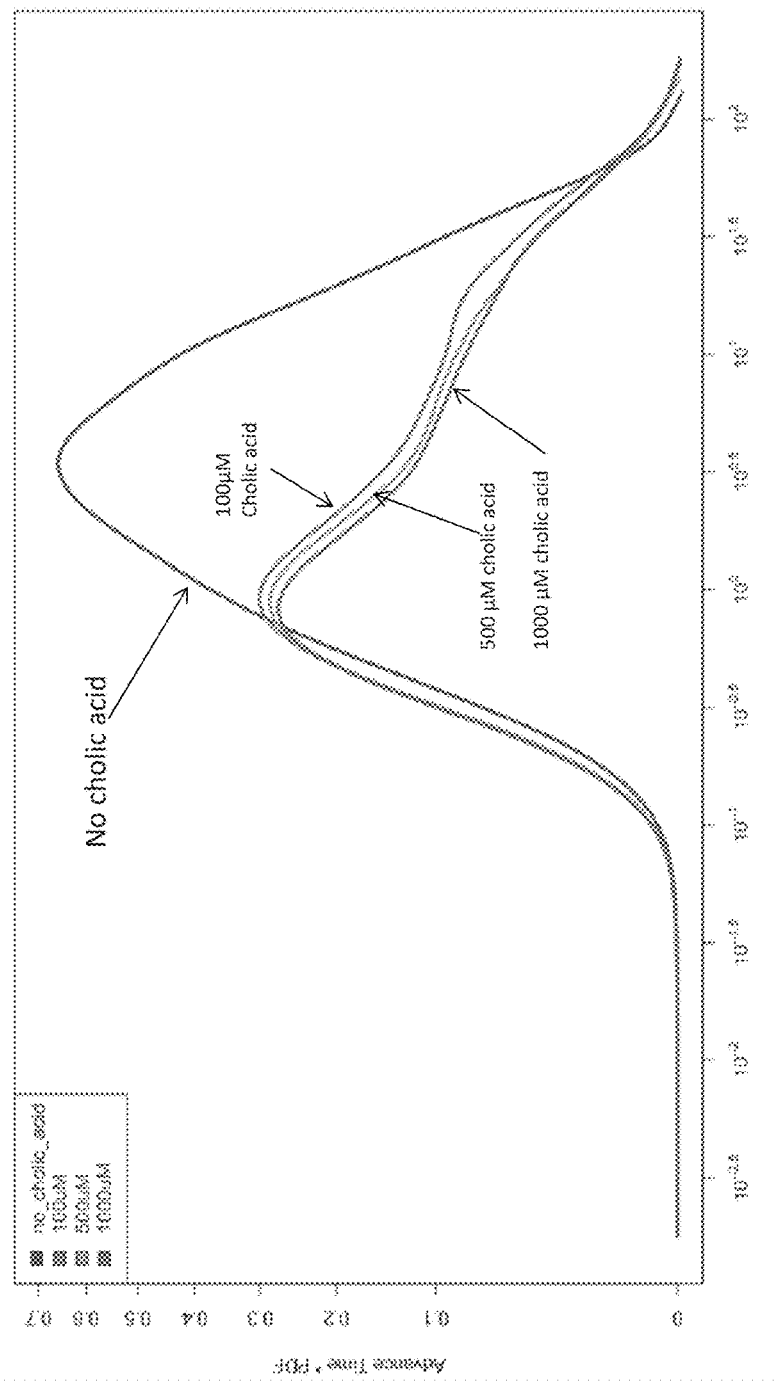
FIG. 18 shows data on the effect of different concentrations of cholic acid on polymerase rate.
Figure 19:
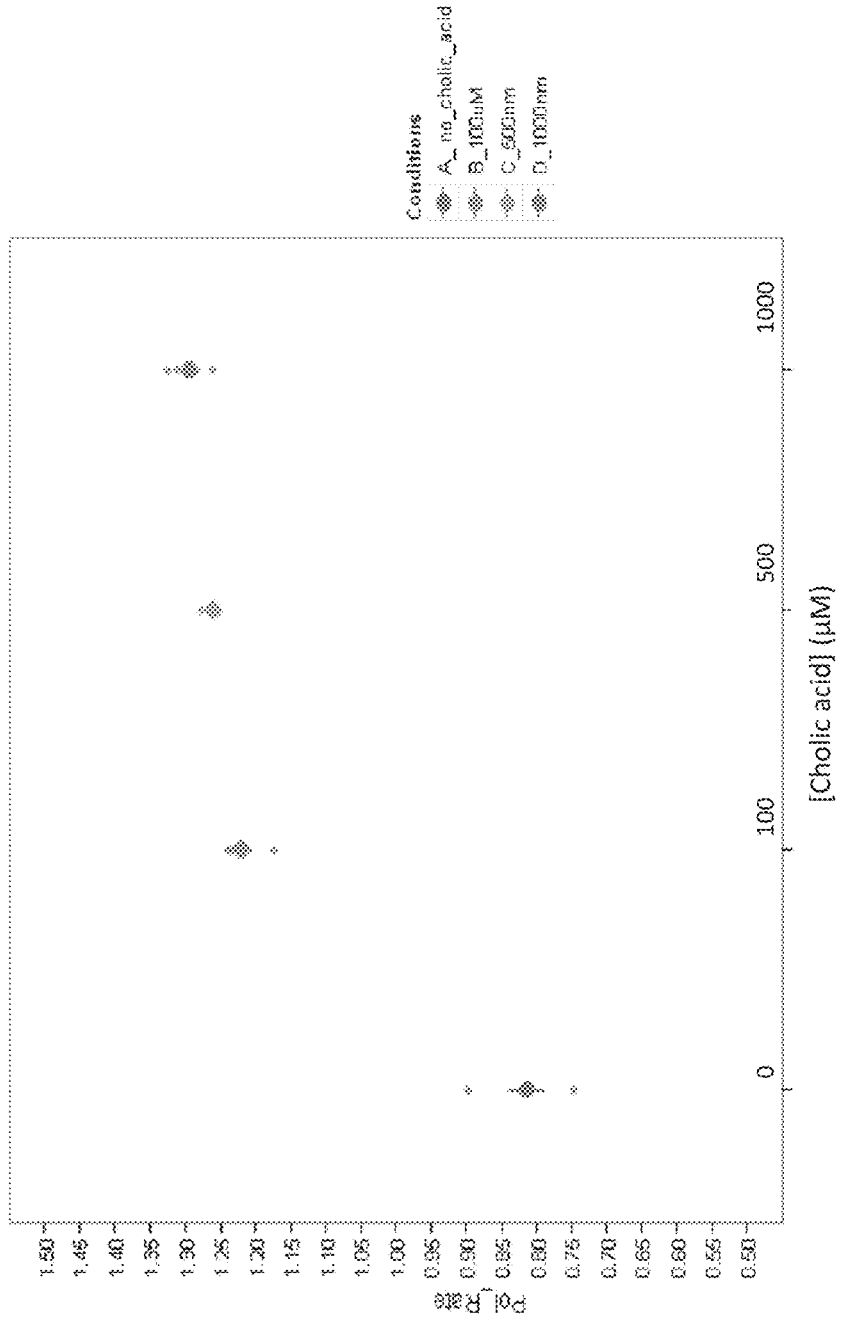
FIG. 19 shows data on the effect of different concentrations of cholic acid on polymerase rate.
Figure 20:
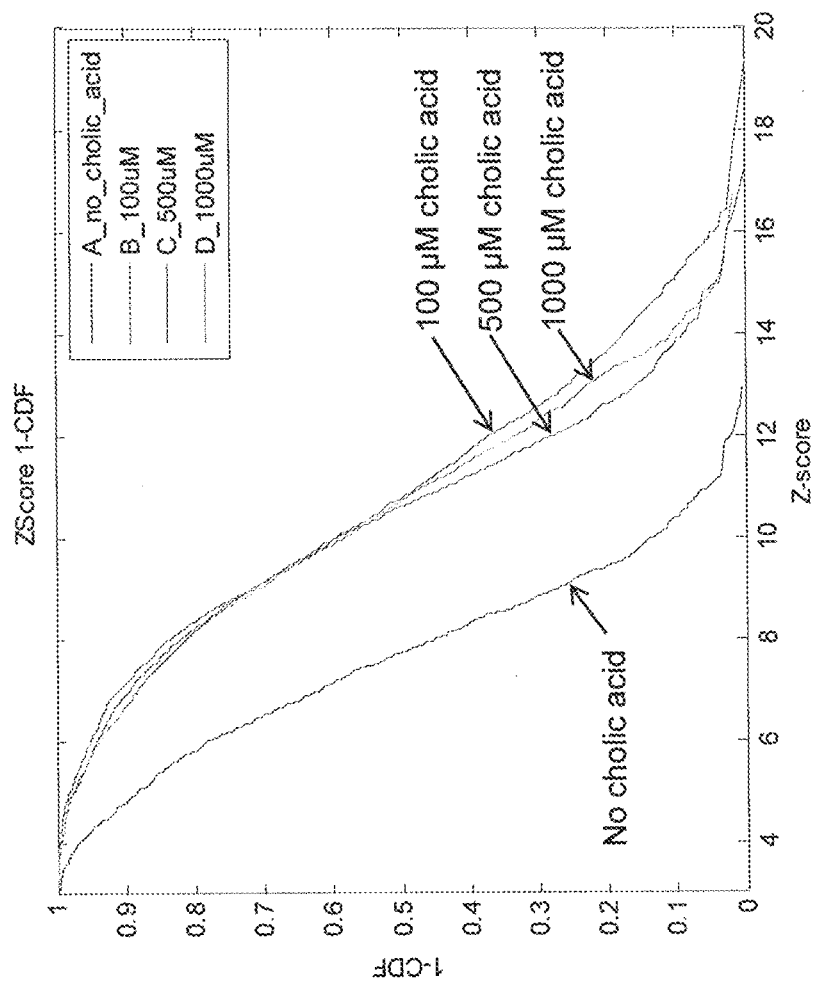
FIG. 20 shows data on the effect of cholic acid on read length.

In further embodiments, methods and compositions of the invention further have the effect of reducing the interpulse distance of lipophilic FRET analogs. Data showing the effects of compositions using cholic acid on interpulse duration are shown in FIGS. 18 and 19. Effect of cholic acid on readlength, which is reflective of IPD, is shown in FIG. 20.

In accordance with any of the above, methods of the invention utilize compositions comprising one or more cholesterol or cholic acid derivatives described herein in concentrations of about 100-500, 110-400, and 120-300 µM.

Organic Solvents

Figure 13:
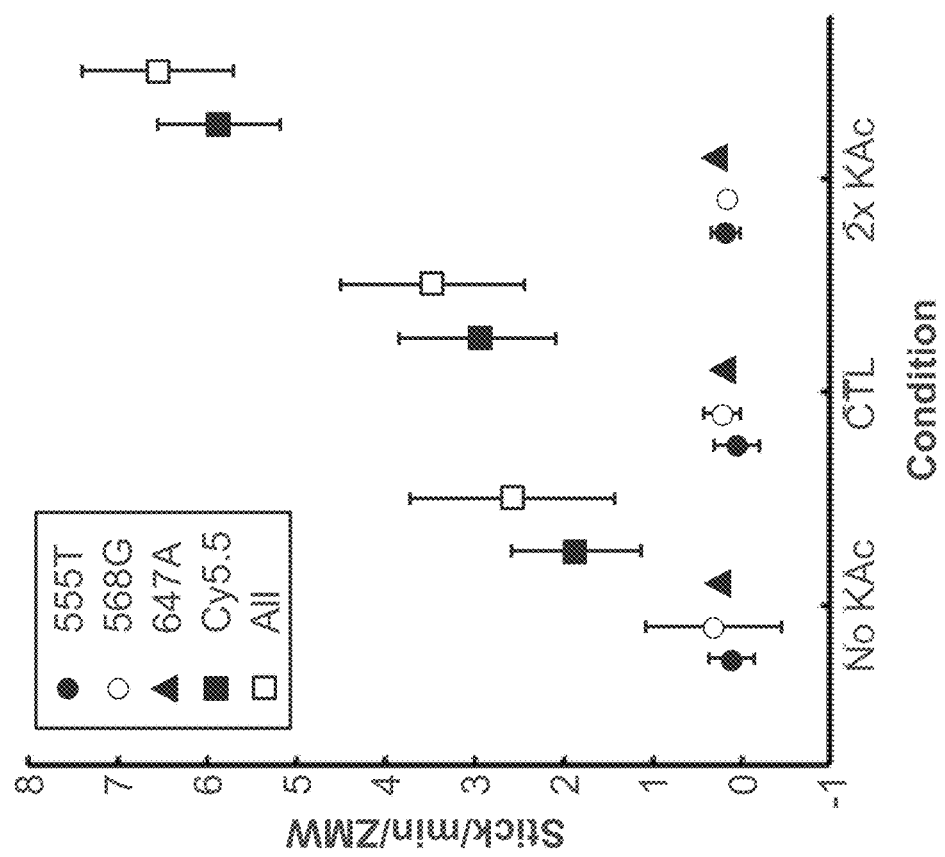
FIG. 13 shows data on non-specific interaction or "sticks" between dye-labeled nucleotides and a surface in solutions of differing ionic strength.

One potential cause for non-specific binding of dye-labeled nucleotides (also referred to herein as analogs) may be through hydrophobic interactions between the analogs and components of the reaction, including the surface upon which the reaction takes place. For example, FIG. 13 shows that non-specific interaction ("sticks") between analogs and PEG-coated silicon dioxide surface increases with ionic strength of the solution.

One aspect of the present invention includes additives that can weaken the hydrophobic interaction between analog and surface, thus reducing the "stick" rate and errors that can result from such non-specific binding. Organic solvents, including without limitation DMF, are of use in accordance with this aspect of the invention.

Figure 14:
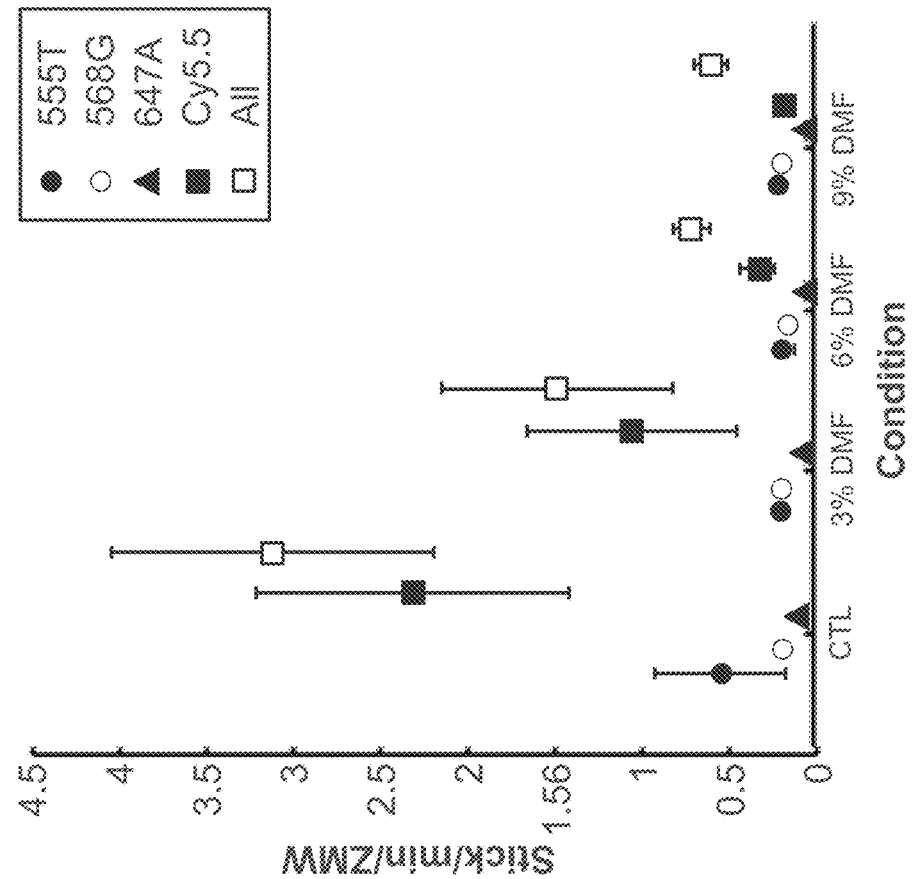
FIG. 14 shows data on the effect of increasing DMF concentration on non-specific interactions between nucleotide analogs and a surface.
Figure 15:
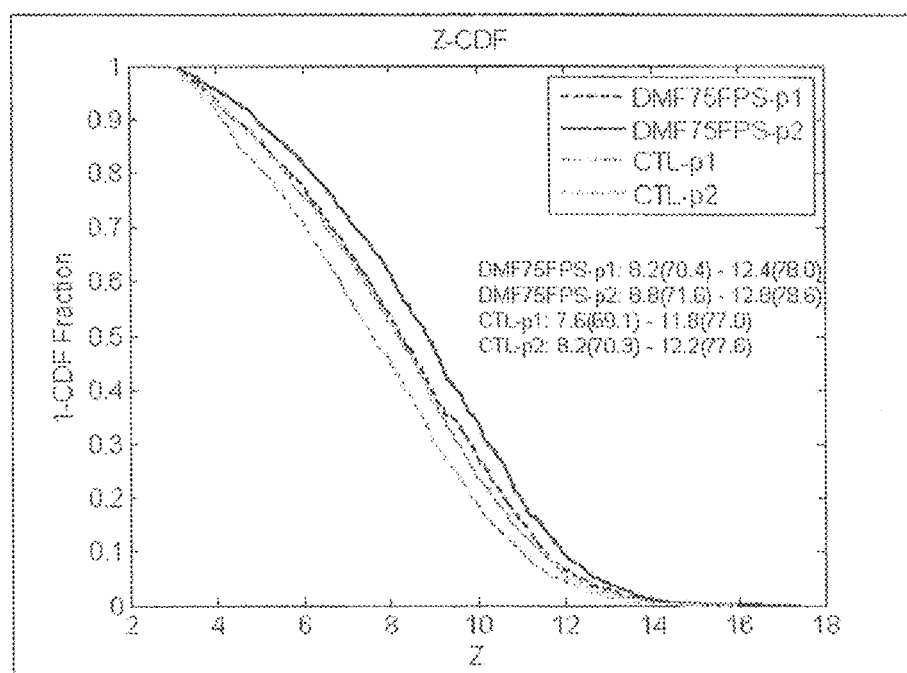
FIG. 15 shows data on the effect of organic solvent during sequencing.

FIG. 14 shows that stick rate decreases with increasing DMF concentration. FIG. 15 shows further studies with DMF—sequencing with DMF resulted in an accuracy gain, which can be attributed to reduction of stick pulses. The data are from an experiment in which eight chips were sequenced at control conditions without organic solvent and another eight chips were sequenced with 6% DMF. The figure is a cumulative distribution function (CDF) of Z-score, in which higher Z-score means better sequencing alignment or accuracy. The "p1" and "p2" in the legend show the average data from two consecutive movies taken from each chip. Among the four CDF curves, the two from chips sequenced with DMF show higher CDF fraction number at high-Z-score range, which means they have higher Z score and accuracy.

In addition to mitigation of non-specific binding of dye-labeled nucleotides, organic solvents can also improve the photophysical characteristics and behavior of fluorescent dyes. For example, in certain aspects, the presence of one or more organic solvents improves fluorescent dye intensity. In further aspects, addition of one or more organic solvents results in improved fluorophore photostability. Without being bound by theory, it is conceived that the enhancement of photostability itself may underlie the observed increase in dye intensity.

Organic solvents that may be included in compositions of the invention include, without limitation, tetrahydrofuran (THF), ethyl acetate, acetonitrile, dimethyl sulfoxide (DMSO), dioxane, dimethylformamide (DMF), dimethylacetamide (DMA), formamide, N,N-(2-hydroxyethyl)formamide, N-pyridine-3-formamide, formyl morpholine, methylpyrrolidone, N-methyl-2-pyrrolidone (NMP), t-butanol, ethanol, ethylene glycol, glycerol, n-propanol, isoproponal, acetic acid, and others described in the art, e.g., in U.S. Pat. No. 6,242,235, incorporated herein by reference in its entirety for all purposes. Further, detergents may be included in compositions of the invention, and some such detergents are further described in the art, e.g., in U.S. Patent Publication Nos. 2011/0312035 and 2010/0099150, both of which are incorporated herein by reference in their entireties for all purposes. Yet further, surfactants and/or polymer additives, such as polyethylene glycol, may also be included in compositions of the invention.

Additives that Reduce Aberrant Enzyme Activity

Aberrant enzyme activity can be caused by various different conditions within an analytical reaction. For example, instability of an enzyme complex, steric hindrance, charge interactions, and sticking of reaction components to surfaces of a device are only a few conditions that can lead to aberrant enzyme activity, which can be detected as, e.g., lower or variable enzyme activity (e.g., reduced catalytic rates, less efficient substrate binding, slower incorporation and/or translocation rates, or altered error profiles (e.g., more or different types of errors)), polymerase pausing (i.e., reduced halting of incorporation of nucleotides into a nascent nucleotide strand by a polymerase), or other changes in the kinetics of catalytic activity. As noted above, interpulse duration (IPD) is one measure of enzyme activity that can be positively affected by addition of one or more of the additives described herein. In certain embodiments, IPD is the period of time following incorporation of a nucleotide and prior to binding of a subsequently incorporated nucleotide in a sequencing by synthesis reaction. Polymerase pausing can also be mitigated by addition of one or more of the additives described herein.

In certain aspects, the invention addresses increased IPD due to use of bulky nucleotide analogs in a polymerization reaction. Long or variable IPD can limit the readlength and affect the error profile of a polymerase enzyme. For example, a polymerase that is slow to translocate and/or bind a new nucleotide analog after incorporation will not incorporate as many nucleotides during a given time period as a polymerase that has a more rapid translocation and substrate binding rate.

Figure 7:
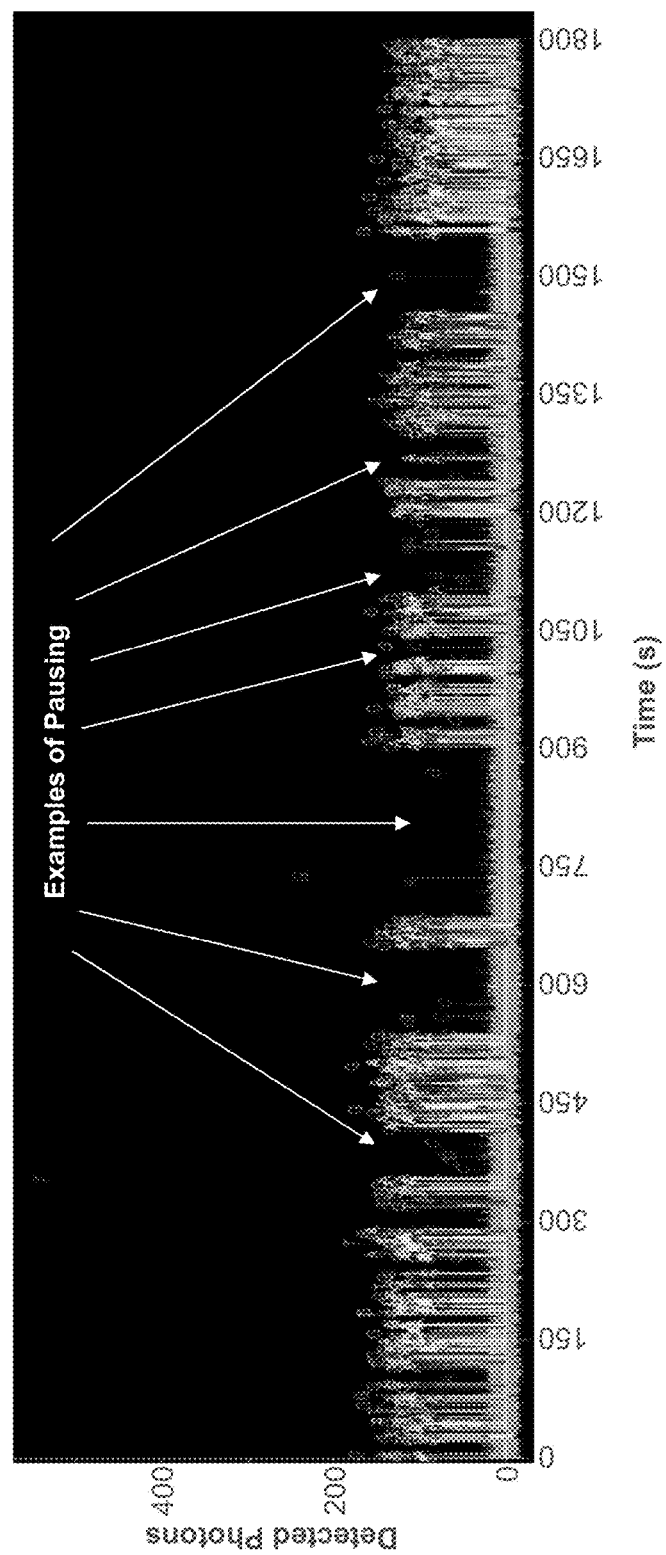
FIG. 7 illustrates examples of polymerase pausing in sequencing data.
Figure 8:
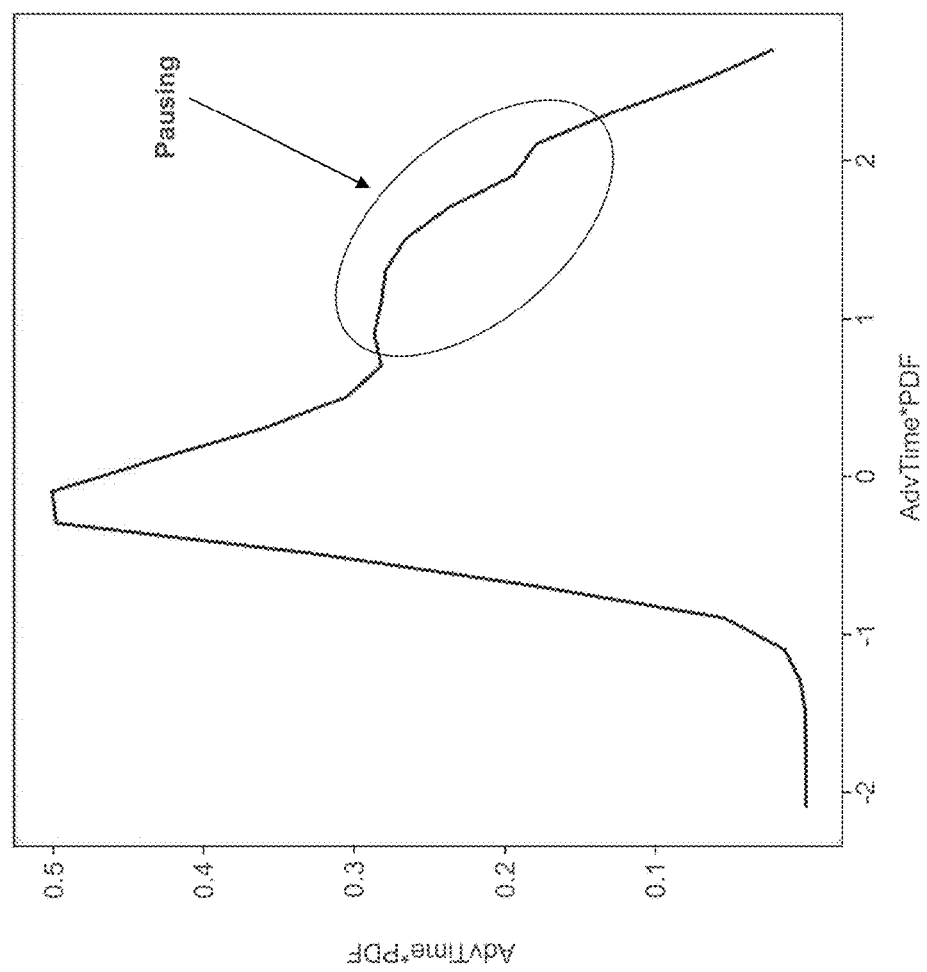
FIG. 8 illustrates an example of polymerase pausing depicted by an accounting stall report metric.

In certain aspects, the invention addresses polymerase pausing, which can limit the readlength in single molecule sequencing methods. For example, many sequencing traces demonstrate periods of time in which the polymerase enzyme ceases functioning for a period of time prior to resuming normal nucleotide incorporation. An example of polymerase pausing within a SMRT® sequencing trace is shown in FIG. 7.

Certain additives of the invention include additives that reduce polymerase pausing, thereby functioning as "pausing reducers." Some additives of the invention include additives that mitigate aberrant enzyme activity other than pausing, e.g., increased IPD, thereby functioning as "kinetic improvers." Although the following description describes additives of particular utility in reduction of aberrant enzyme activity, it will be appreciated that the following additives may also be used for reduction of background signal noise by reduction of non-specific adsorption of reagents to components of a reaction, as are other additives described herein. In addition, additives described herein as being useful for reduction of background signal noise may also be used to reduce aberrant enzyme activity.

In accordance with any of the above, additives of the invention include amino acids. In specific embodiments, additives of the invention include charged amino acids such as arginine and glutamate. In exemplary embodiments, amino acids such as arginine are included in compositions of the invention as a bulk additive to reduce polymerase pausing. Although the following discussion focuses on arginine as an additive, it will be appreciated that any amino acid, particularly other charged amino acids and amino acids with similar side chains to arginine, can be used in accordance with the discussion herein.

Figure 9:
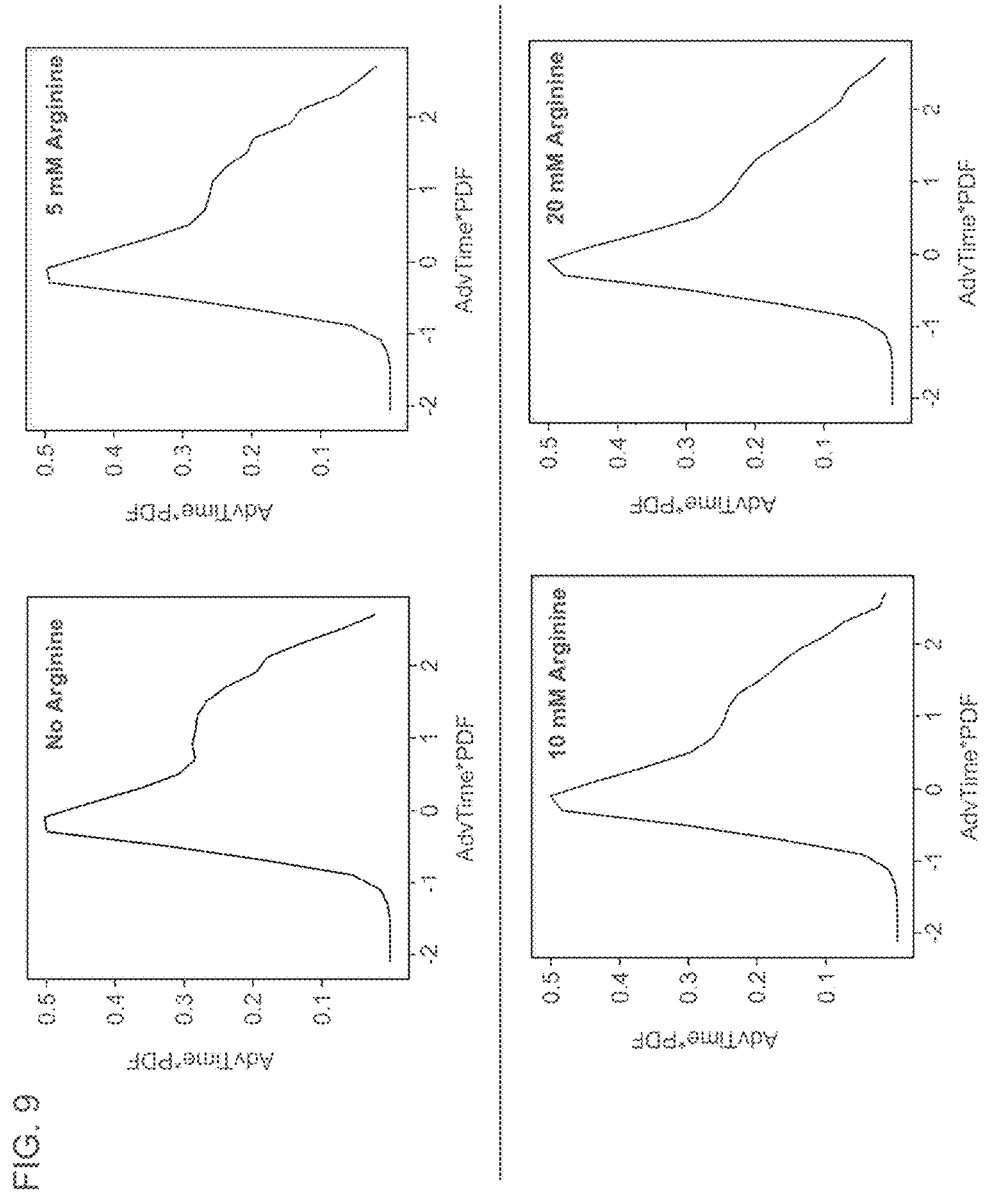
FIG. 9 shows data on the effect of arginine on polymerase pausing depicted by an accounting stall report metric. The X and Y axis of each of the graphs in FIG. 9 are the same as those in FIG. 8.

In specific embodiments of the invention, use of arginine as an additive in compositions of the invention serves to reduce polymerase pausing. When the amount of arginine additive was increased, reduction of enzymatic pausing was observed (FIG. 9). Without being bound by theory, one possible mechanism for action of the effect of arginine is that its charged side-chain containing a conjugated —$NR_3$ moiety may be responsible for pausing reduction. In some embodiments, arginine is included in compositions of the invention in concentration ranges of from about 1 mM to 100 mM. In certain embodiments, arginine is included in concentrations of from about 20-40 Mm. In further embodiments, arginine is included in a concentration of about 30 mM. In still further embodiments, arginine is included in concentrations in ranges of about 1-150, 10-140, 20-130, 30-120, 40-110, 50-100, 60-90, 70-80 mM.

In further embodiments, oligopeptides of from about 2-20 amino acids are used as additives in compositions of the invention. In exemplary embodiments, such oligopeptides include at least one arginine residue. In still further embodiments, such oligopeptides include at least 2, 3, 4, 5, 6, 7, 8, 9, 10, 11, 12, 13, 14, 15, 16, 17, 18, 19 or 20 arginine residues.

In still further embodiments, compounds similar to the side-chain of arginine, such as guanidine and its derivatives, can also be used in accordance with the present invention as additives. In yet further embodiments, compounds similar to guanidine (i.e. urea and its derivatives) may also be used as additives.

Figure 10:
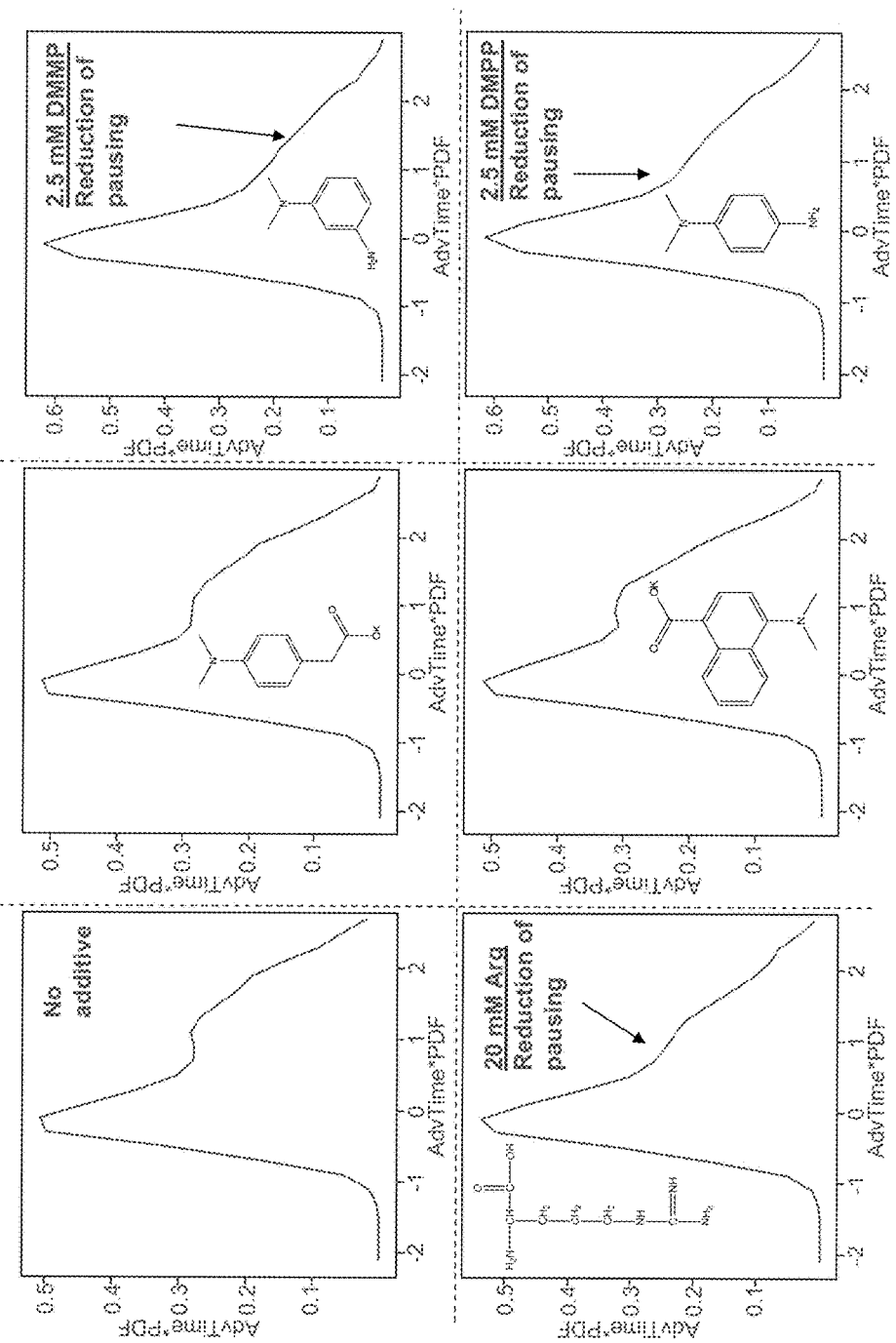
FIG. 10 shows data on the effect of DMMP and DMPP on polymerase pausing depicted by an accounting stall report metric. The X and Y axis of each of the graphs in FIG. 10 are the same as those in FIG. 8.

In one aspect of this invention, compounds comprising an aromatic ring and two —NR2 substituents may be useful as additives for reducing polymerase pausing. For example, N,N-dimethyl-m-phenylenediamine (DMMP) or N,N dimethyl-p-phenylenediamine (DMPP) both demonstrated pausing reduction (FIG. 10). In certain embodiments, such additives are present in a concentration range of from about 0.1 mM to about 50 mM. In further embodiments, additives comprising an aromatic ring and two —NR$_2$ substituents are present in a concentration range of from about 1 mM to about 10 mM. In a yet further embodiment, such additives are present in a concentration of about 1.0, 2.0, 2.5, 3.0, 3.5, 4.0, 4.5, 5 mM. In still further embodiments, additives comprising an aromatic ring and two —NR$_2$ substituents are present in a concentration range of 0.01-100, 0.1-90, 0.5-80, 1-70. 10-60, 20-50, 30-40 mM.

In addition to pausing reduction capabilities, additives of the invention, including additives comprising an aromatic ring and two —NR2 substituents, can further serve as quenchers of the reactive triplet state.

Figure 11:
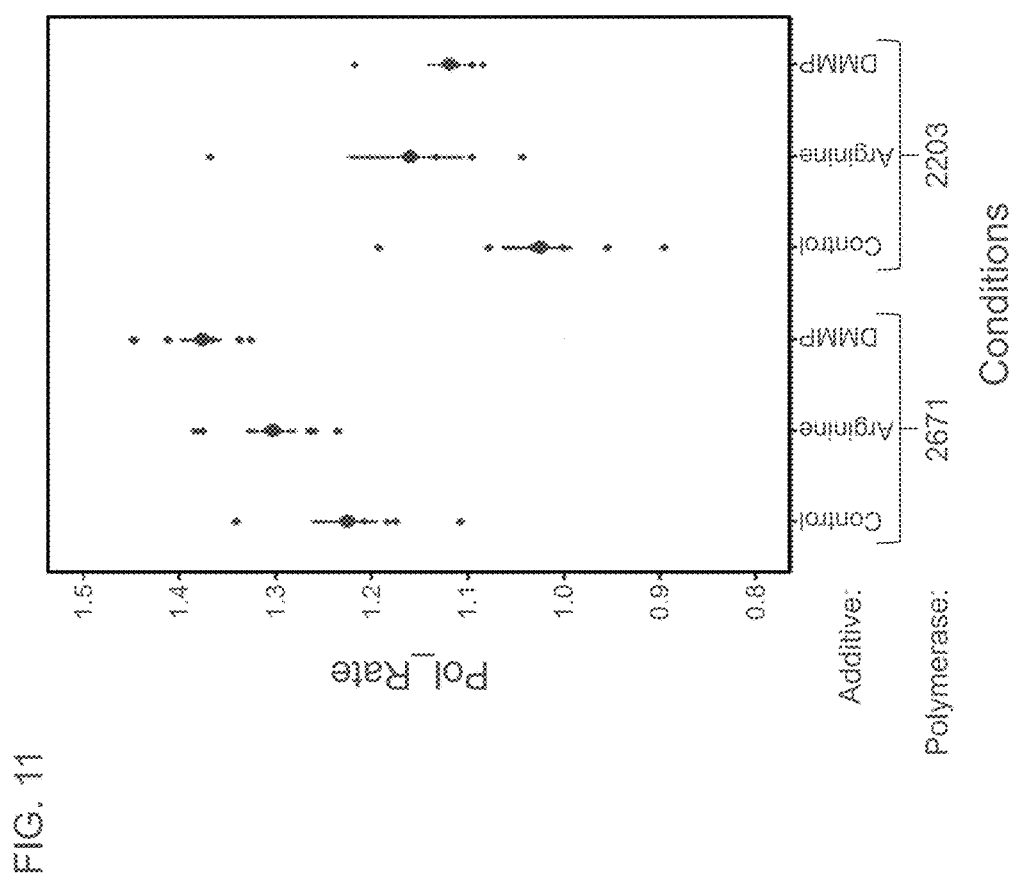
FIG. 11 shows data on the effect of arginine and DMMP on pausing reduction an polymerase rate increase for different polymerases.

The effect of pausing reduction on polymerase rate by both Arg and DMMP additives is demonstrated in FIG. 11.

Figure 12:
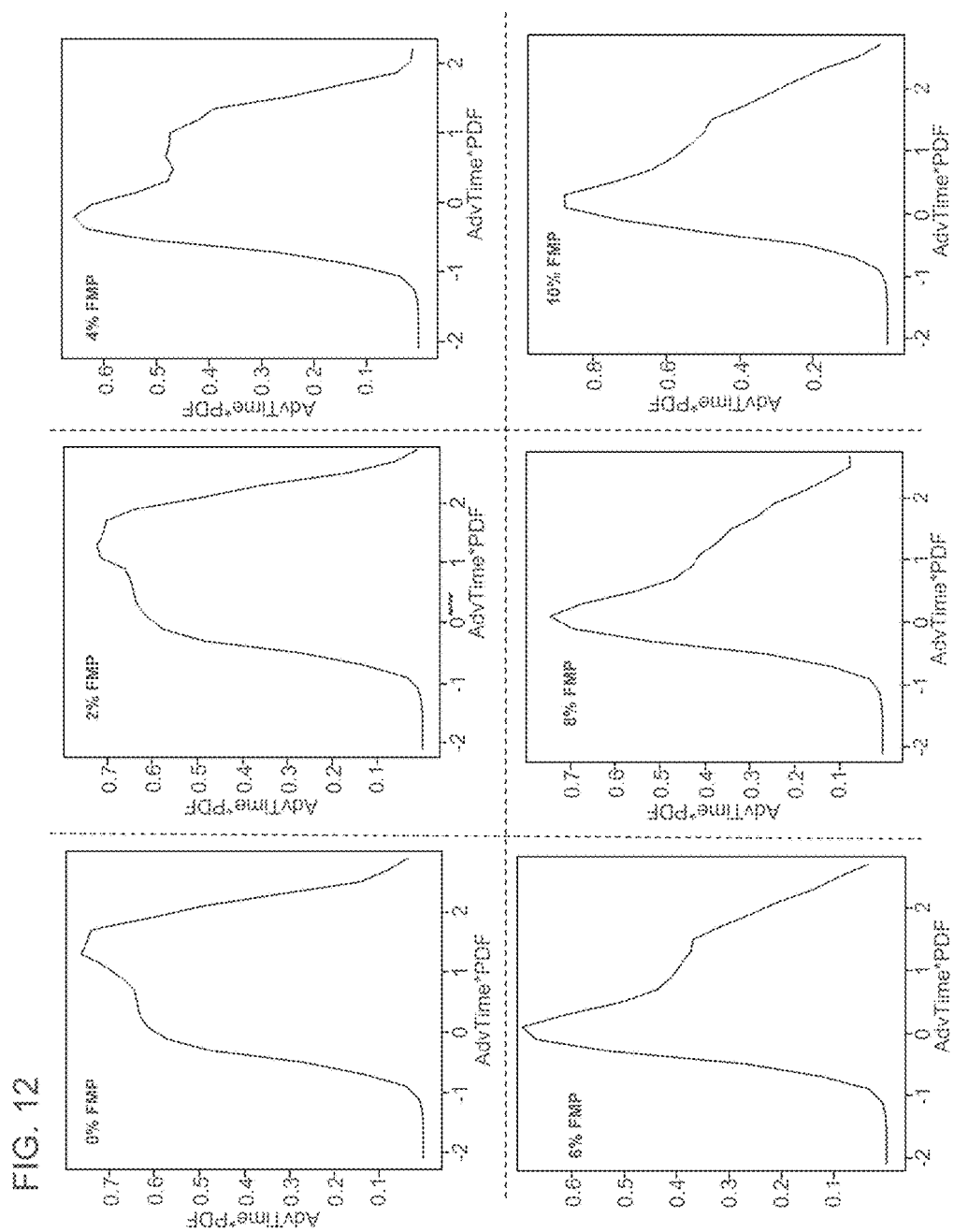
FIG. 12 shows data on the effect of FMP on polymerase pausing. The X and Y axis of each of the graphs in FIG. 12 are the same as those in FIG. 8.

In yet another aspect of this invention, morpholine derivates, including without limitation N-formylmorpholine (FMP), are used as additives to reduce polymerase pausing. Decrease of pausing with increase of FMP concentration is shown in FIG. 12. In certain embodiments, a concentration range of from about 0.1% to 20% by volume of morpholine derivatives are used in accordance with the present invention. In further embodiments, 2-10% by volume concentration range is used. In a yet further embodiment, a concentration of about 2, 3, 4, 5, 6, 7, 8, 9, 10% by volume is used. In a still further embodiment, a concentration range of from about 0.1-30, 0.5-25, 1.0-20, 1.5-15, 2.0-10, 2.5-5% by volume is used.

In further aspects of the invention, other organic solvent additives are used as additives in compositions of the invention to reduce polymerase pausing.

In accordance with any of the above, additives of the invention include cholesterol or cholic acids and derivatives thereof. In specific embodiments, such additives of the invention include taurocholic acid and sulfonic cholic acid derivatives, cyclodextrin and derivatives thereof, and dT oligonucleotides. In exemplary embodiments, such compounds are included in compositions of the invention as a bulk additive to reduce aberrant enzyme activity, and in specific embodiments, to reduce IPD, e.g., where bulky nucleotide additives are used. When measuring over a plurality of single molecule reactions, IPD values are a distribution, so some variability exists from each reaction to the next. However, when using certain nucleotide analogs, e.g., bulky analogs having large labels, e.g., FRET labels, that distribution shifts toward longer IPD values. Inclusion of these additives within the reaction mixture pushes the distribution back toward shorter IPD values. For example, addition of cholic acid derivatives such as taurocholic acid and sulfonated cholic acid derivatives reduces IPD values for polymerase-mediated single-molecule sequencing reactions using nucleotide analogs comprising multi-dye constructs, e.g., FRET dyes. Similar effects are detected when poly dT oligonucleotides, cyclodextrin, or cyclodextrin derivatives are added.

Cyclodextrin

The present invention provides methods of employing cyclodextrin compositions in the performance of solid phase enzyme reactions and particularly those solid phase reactions that utilize labeled reactants, such as fluorescently labeled reactants. For example, cyclodextrin compositions can be employed as kinetic improvers, as described above. The cyclodextrin compositions utilized in the methods of the invention preferably include substituted cyclodextrins that are preferably present as substantially isomerically pure compositions.

In certain particular aspects, the methods of the invention comprise providing an observation region for monitoring a reaction of interest, providing in the reaction region a reaction mixture that includes first and second reactants that react in the reaction of interest, where at least one the first and second reactants comprises a detectable property, and a cyclodextrin composition of the above structure, whereby the cyclodextrin is present at a concentration that reduces non-specific interactions between the reactant having the detectable group and other reaction components present in the observation region.

Exemplary reactions include binding reactions, catalytic reactions, and synthetic reactions where one component of such reaction bears a detectable property such as a labeling group or the like. Binding reactions, for example, typically employ a first component that is immobilized upon a solid support such as a matrix, or solid surface of a substrate. A detectable reagent that is being tested for its ability to bind the first reagent is then exposed to the solid support, and the resulting system is washed to remove any unbound detectable reagent. Any remaining detectable reagent is thought to be bound to the first immobilized component. Such binding reactions are widespread in analyses, including for example, antibody/antigen assays, nucleic acid hybridization assays, ligand/receptor assays, and myriad others. As will be appreciated any nonspecific adsorption of the detectable component to the overall system, e.g., either the underlying solid support or the reaction component that is bound to the underlying substrate, will yield a level of background signal or noise that is not relevant to a determination of specific binding. Such background noise reduces the overall sensitivity of the analysis.

Examples of cyclodextrin compositions for use in the methods of the invention include those compositions that have been previously described for use as chiral resolving agents (See, e.g., U.S. Pat. No. 6,391,862, which is incorporated herein by reference in its entirety for all purposes and in particular for all teachings related to chiral resolving agents). Variations on such compositions are also included within the methods and compositions of the invention, as described in greater detail herein.

Without being bound to a particular theory of operation, it is believed that these compositions serve to block potential non-specific binding sites on other reaction components, e.g., underlying substrates or solid supports, proteins, or the like, which are believed to provide association sites for the detectable reagents used in these analytical operations, or the by-products of these reagents, contributing to interfering signal noise. It is believed that the noise contributed by this nonspecific interaction is reduced or eliminated by blocking these non-specific association sites using the compositions described herein, as shown by the consequent improvement in signal to noise ratios and other reaction quality metrics.

As noted above, exemplary structures of the compositions used in the methods of the invention include those set forth in U.S. Pat. No. 6,391,862, previously incorporated herein, such as sulfated cyclodextrins, and variations of such compositions. In general, the compositions used in the methods described herein have the structure:

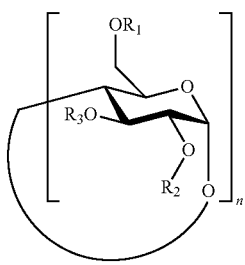

where n is from 6 to 12, R1 is a group that is non-attractive to the detectable component of the reaction of interest, i.e., neutral or repulsive with respect to the detectable component of the reaction of interest. For example, where the detectable component of the reaction of interest is charged, then R1 would preferably be uncharged or would bear a common charge, e.g., positive to positive. Likewise, where the detectable reaction component is hydrophobic, then R1 may be hydrophilic, so as to repel the detectable reaction component, or vice versa.

For certain compositions used in the methods of the invention, R2 and R3 are selected to provide an associative group with respect to the non-specific binding sites on other reaction components that are sought to be blocked or masked, e.g., solid support surfaces, proteins, etc. For certain applications, where the nonspecific binding sites comprise hydrophobic groups, e.g., on the surface of a substrate or other solid support that has hydrophobic characteristics, then R2 and R3 would preferably be hydrophobic groups to associate with and block such surface groups from associating with detectable reaction components. Likewise, if the non-specific binding sites are charged, then R1 and R2 would preferably be oppositely charged to associate with and block such groups.

A wide variety of charged groups may be selected to provide the requisite association or repulsion for the various groups on the compositions described herein. For example, where any or all of R1, R2 and R3 are negatively charged groups, they are preferably selected from such negatively charged groups as sulfate, phosphate, carboxylate, and the like.

Where any or all of R1, R2 and R3 are positively charged groups, they are preferably selected from such groups as ammonium, quaternary amine, and the like.

Where any or all of R1, R2 and R3 are hydrophobic groups, they are generally selected from groups such as alkyl, e.g., C1-C12, hydroxyalkyl, e.g., C2-C8, a acyl, e.g., C2-C12, aryl, carbamate, a thiocarbamate, carbonate, silyl, ester, or combinations thereof.

As will be appreciated, the selection of R1, R2 and R3 groups can depend upon both the nature of the nonspecific binding groups and the nature of the detectable reaction components, which also can be related. In particular, where a detectable reagent is positively charged, it can non-specifically associate with negatively charged groups on the surface of a solid support. In conjunction with the invention then, the R2 and R3 groups may be selected to be positively charged groups to associate with the negatively charged surface groups. In addition, the R1 group would be selected to be non-attractive to the detectable reaction component. In the case of a positively charged detectable reaction component, a positively charged R1 group may be used.

In order to ensure that the cyclodextrin compositions of the invention are consistently oriented to present the desired characteristics to the desired environment, e.g., presenting hydrophobic groups to a surface while presenting a negatively charged group to the reaction mixture, it is preferable that such mixtures exist as a substantially isomerically pure composition. Preferably, the cyclodextrin composition has an isomeric purity of at least 80 mole %, with an isomeric purity of at least 90 mole % being more preferable, and an isomeric purity of at least 95 mole % being even more preferable. Methods for deriving cyclodextrin compounds of sufficient purity are known in the art and are described, for example, in U.S. Pat. No. 6,391,862, previously incorporated here by reference.

In certain particularly preferred aspects, R1 is $SO_3^-$ while R2 and R3 are hydrophobic groups, such as alkyl, hydroxyalkyl, acyl, CH2-acyl, and acetamide groups, including, for example diethylacetamide groups, dipropylacetamide, and the like, as well as aryl or heteroaryl groups such as morpholino, piperazine, piperidine, pyrrolidine, oxazolidine, and the like.

For example, in certain particularly preferred aspects, the methods of the invention comprise nucleic acid analyses where the detectable reaction component comprises a nucleic acid, or nucleoside polyphosphate, and the reaction is carried out at or proximal to a substrate surface. Accordingly, the compositions used in such preferred methods would typically include a negatively charged group in the R1 position, such as a sulfate group. In addition, the R2 and R3 groups would preferably be selected to associate with the substrate surface. For underivatized silica substrates that bear a substantially negative surface charge, positively charged R2 and R3 groups would be preferably selected. For derivatized surfaces that bear hydrophobic groups however, R2 and R3 would generally be selected from hydrophobic substituents.

Examples of compounds according to the particularly preferred aspects of the present invention include, e.g., heptakis(2,3-diacetylmorpholine-6-sulfato)-β-cyclodextrin (Compound 1), and heptakis(2,3-diacetyldiethylacetamide-6-sulfato)-β-cyclodextrin (Compound 2). These compounds are illustrated with reference to FIG. 1 which shows a sulfated cyclodextrin molecule with substitutions of morpholine and diethylacetamide for the 2'-OH and 3'-OH positions.

Figure 17:
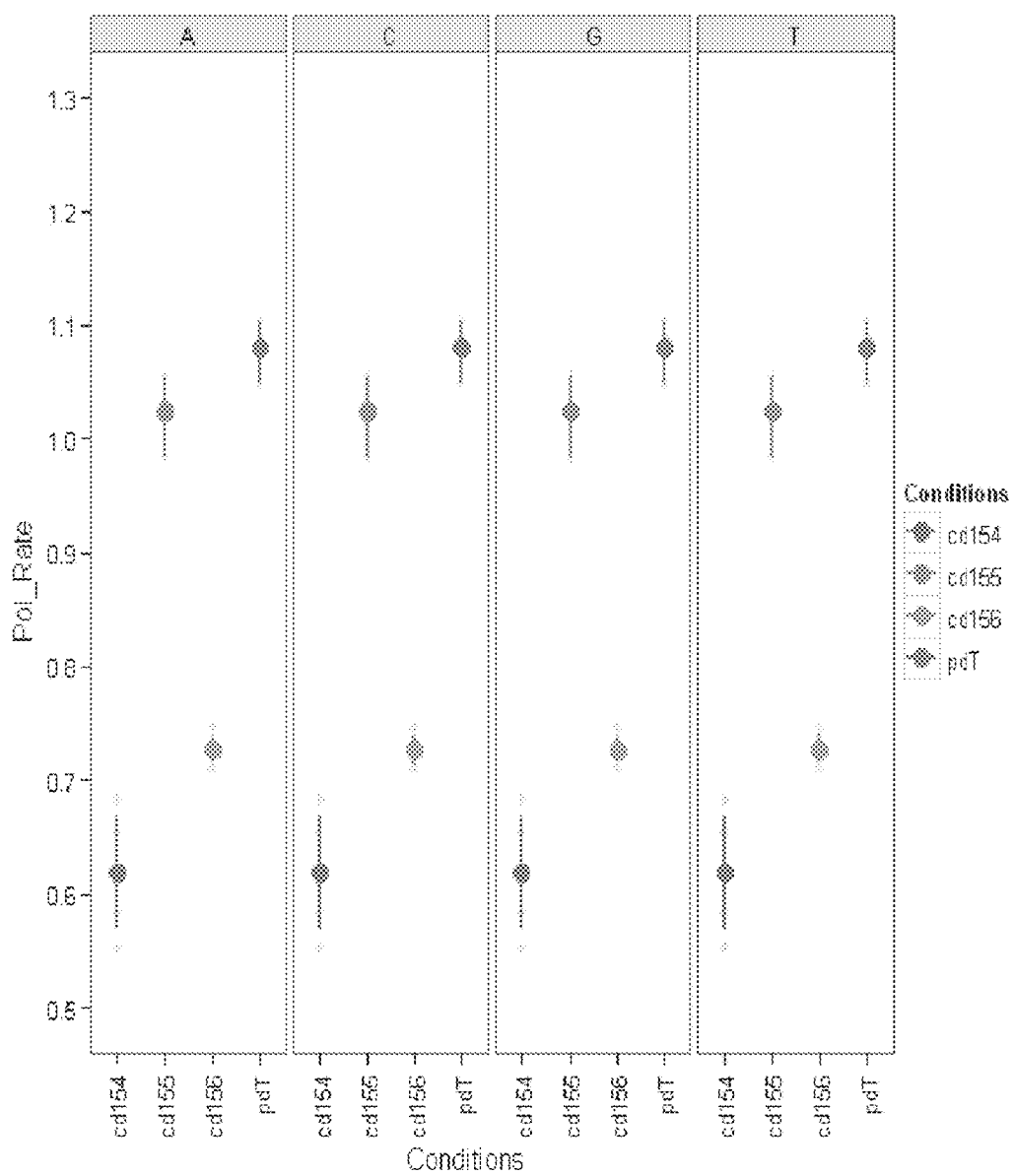
FIG. 17 shows data on the effect of cyclodextrin compounds of the invention on polymerase rate.

As discussed above, interpulse duration (IPD) is one measure of enzyme activity that can be positively affected by addition of one or more of the additives described herein. In certain embodiments, IPD is the period of time following incorporation of a nucleotide and exit of a labeled polyphosphate, and prior to binding of a subsequently incorporated nucleotide in a sequencing-by-synthesis reaction. In certain embodiments, cyclodextrin compounds of the invention affect interpulse duration, which can be reflected in polymerase rate, as shown in FIG. 17 for various cyclodextrin compounds of the invention (which are illustrated in FIG. 16). The following table further provides data on the effect of various cyclodextrin compounds of the invention on readlength, which is reflective of reduced IPD and increased polymerase rate:

|  | Poly dT | SY360-154 | SY360-155 | SY360-156 |
|---|---|---|---|---|
| Median Z-score | 17.92 | 17.34 | 18.23 | 13.13 |
| Median Accuracy | 86.84% | 86.91% | 87.34% | 81.36% |
| Median Readlength | 564 bp | 356 bp | 504 bp | 376 bp |
| # of reads with Z > 3 | 1274 | 957 | 974 | 844 |
| Median Accuracy | 87.22% | 87.22% | 87.94% | 82.57% |
| Median Readlength | 566 bp | 356 bp | 508 bp | 379 bp |
| # of bases with QV >=6 | 662228 | 303565 | 470277 | 259236 |

Additional Components and Formulations for Compositions of the Invention

As will be appreciated, in addition to the additives discussed above, compositions of the invention may further include components useful to analytical reactions, particularly sequencing reactions. Such components are known in the art and can include without limitation (singly or in any combination): nucleotides or nucleotide analogs, buffers such as phosphate, citrate, other organic acids, MOPS, bis-tris propane (BTP); antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EGTA or EDTA; reducing agents such as DTT, sugars such as sucrose, mannitol, trehalose or sorbitol; salt-forming counter-ions such as potassium, sodium, magnesium, and strontium; metal complexes (e.g. Zn-protein complexes); non-ionic surfactants such as TWEEN™, PLURONICS™ or polyethylene glycol (PEG), and/or coenzymes such as ATP. In certain preferred embodiments at least 1, 2, 3, 4, 5, or 6 or more of the above components are used in combination with the additives described elsewhere herein.

In further embodiments, compositions of the invention include the additives discussed herein and any combination of one or more other reaction components known in the art and discussed for example in WO/2010/144150; WO/2009/114182; WO/2009/102470; WO/2011/112260; U.S. Pat. No. 7,767,394; U.S. Pat. No. 7,405,281; US 2012/0009567; US 2007/0128133; US 2010/0167299, each of which is hereby incorporated by reference in its entirety for all purposes and in particular for all teachings related to components of compositions used in analytical reactions such as sequencing reactions.

In still further embodiments, compositions of the invention comprise components according to the following general formulation:

General Formulation

| | |
|---|---|
| Tris-type buffer (pH 7.5-8.0) to stabilize reaction pH | 20-30 mM |
| Salt, e.g., KOAc, LiOAc, NH$_4$OAc, to set ionic strength, mitigate protein aggregation, and/or modify rate of catalysis by competition with cofactor (In further embodiments, multiple salts are included. In still further embodiments, LiOAc is included at a lower concentration, e.g., less than 1 mM) | 120 mM |
| Enzyme cofactor; sets rate of catalysis, e.g., MgOAc or MnOAc | 25-30 mM |
| Reducing agent/photodamage mitigator, e.g., DTT, MEA (can be used separately or in combination, e.g. with DTT at 40 mM and MEA at 10 mM) | 10-40 mM |
| Anti-pause agent (increases rate of polymerization), e.g., DMAPA, DMPP, DMMP (In alternative embodiments, Arginine is used @ 20-50 mM) | 2.5 mM |
| Anti-sticking agent 1; shortens IPDs; increases rate of polymerization, e.g., taurocholic acid, cyclodextrin-morpholino, poly-dT | 120 µM |
| Anti-sticking agent 2, e.g., FMP, DMF, DMA, DMSO | 2-4% |
| Chelating agent, e.g., EDTA, EGTA (optional) | 3 mM |

As will be appreciated, in further embodiments, the formulation may include a subset of the above listed components in any combination.

The above general formulation may further include any of the other additives discussed herein. In further embodiments, compositions of the invention include one or more components of the above general formulation in combination with other additives, including without limitation additives for photodamage mitigation, such as oxygen scrubbers and triplet state quenchers, and any of the additives described for example in U.S. Pat. No. 7,993,895; U.S. Pat. No. 8,252,911; U.S. Patent Publication No. 20090325260; U.S. Pat. No. 8,388,982; U.S. Patent Publication No. 20120052488; U.S. Patent Publication No. 20120009567 (01-012901); and U.S. Provisional Application No. 61/707,621, filed Sep. 28, 2012, each of which is hereby incorporated by reference for all purposes and in particular for all disclosure, figures or examples related to additives to include in reaction compositions. It will be further understood that where the formulation is to be used for an analytical reaction, components of the analytical reaction will also be present, for example, proteins (e.g., enzymes), cofactors, substrates, competitive agents, inhibitors, agents to initiate and/or terminate the reaction, and other components, whether present at the initiation of the reaction or added subsequent to the initiation.

In still further embodiments, compositions of the invention comprise components according to the following exemplary formulations:

Exemplary Formulation 1

| | | |
|---|---|---|
| Bis-Tris-Propane buffer (pH 8.0) | 25 mM | Stabilizes reaction pH |
| MgOAc | 25 mM | Enzyme cofactor; sets rate of catalysis |
| LiOAc | 0.5 mM | Modifies rate of catalysis by competition with MgOAc |
| KOAc | 120 mM | Sets ionic strength; prevents protein aggregation |

-continued

| | | |
|---|---|---|
| DTT | 40 mM | Reducing agent; mitigates photo-induced damage |
| DMAPA | 2.5 mM | Anti-pause agent (increases polymerase rate) |
| Cyclodextrin-morpholino | 120 µM | Anti-sticking agent; increases accuracy & read length |
| FMP | 4% | Anti-sticking agent |

Exemplary Formulation 2

| | | |
|---|---|---|
| Bis-Tris-Propane buffer (pH 8.0) | 20 mM | Stabilizes reaction pH |
| MgOAc | 25 mM | Enzyme cofactor; sets rate of catalysis |
| LiOAc | 0.5 mM | Modifies rate of catalysis by competition with MgOAc |
| KOAc | 120 mM | Sets ionic strength; prevents protein aggregation |
| DTT | 40 mM | Reducing agent; mitigates photo-induced damage |
| MEA | 10 mM | Reducing agent; mitigates photo-induced damage; TSQ cofactor |
| DMAPA | 2.5 mM | Anti-pause agent (increases polymerase (pol) rate); TSQ cofactor |
| Poly-dT | 120 µM | Anti-sticking agent; increases accuracy & read length |
| DMSO | 4% | Anti-sticking agent |

Exemplary Formulation 3

| | | |
|---|---|---|
| TRIS buffer (pH 8.0) | 30 mM | Stabilizes reaction pH |
| MgOAc | 25 mM | Enzyme cofactor; sets rate of catalysis |
| LiOAc | 0.5 mM | Modifies rate of catalysis by competition with MgOAc |
| KOAc | 120 mM | Sets ionic strength; prevents protein aggregation |
| MEA | 10 mM | Reducing agent; mitigates photo-induced damage; TSQ cofactor |
| DMA | 4% | Anti-sticking agent |

Exemplary Formulation 4

| | | |
|---|---|---|
| ACES buffer (pH 6.5) | 67 mM | Stabilizes reaction pH |
| MnOAc | 0.7 mM | Enzyme cofactor; sets rate of catalysis |
| KOAc | 120 mM | Sets ionic strength; prevents protein aggregation |
| DTT | 120 mM | Reducing agent; mitigates photo-induced damage |
| DMF | 4% | Anti-sticking agent |

As will be appreciated, the above formulations are not meant to be limiting, and one of skill in the art would readily understand that any subset or combination of the above components is encompassed by the present invention. As with the general formulation, the above exemplary formulations may further include any of the other additives discussed herein. In further embodiments, compositions of the invention include one or more components of the above exemplary formulations in combination with other additives, including without limitation additives for photodamage mitigation, such as oxygen scrubbers and triplet state quenchers, and any of the additives described for example in U.S. Pat. No. 7,993,895; U.S. Patent Publication No. 20090325260; U.S. Pat. No. 8,388,982; U.S. Patent Publication No. 20120052488; U.S. Patent Publication No. 20120009567 (01-012901); and U.S. Provisional Application No. 61/707,621, filed Sep. 28, 2012, each of which is hereby incorporated by reference for all purposes and in particular for all disclosure, figures or examples related to additives to include in reaction compositions.

Methods of the Invention

As will be appreciated, the present invention is applicable to a wide variety of analytical reactions where one wishes to monitor that reaction by observing the specific association of a detectable reaction component with another component, e.g., a surface bound component. Such reactions include those where the association, itself, is the outcome of interest in the analysis, such as in binding assays, e.g., antibody/antigen, hybridization assays, e.g., nucleic acid hybridization assays, ligand/receptor binding assays, and incorporation assays, where a labeled reactant is wholly or partly incorporated into a product of the reaction, thus rendering the product detectable.

Notably, however, the methods of the invention are also applicable to reactions where the association event is a transient prerequisite to the reaction of interest, but does not necessarily survive into the product of the reaction of interest. Such reactions include, for example, real time reactions that observe the reactions of interest while they occur. Such reactions include, e.g., real time monitoring of polymerization reactions, and the like, where the detectable component is not, itself, incorporated into the product. Such reactions include single molecule real time detection of biological reactions such as nucleic acid replication, translation and transcription, e.g., as described in Eid et al., Science Vol. 323 no. 5910 pp. 133-138 (January 2009), and Uemura et al., Nature 464, 987-988 (April 2010), each of which is hereby incorporated by reference in its entirety for all purposes and in particular for all teachings related to single molecule real time detection of biological reactions.

As will be appreciated, the observation of the association event of interest is rendered more difficult by the presence of interfering background signals presented by non-specifically associating detectable molecules. In particular, if detectable reaction components non-specifically interact with other components of the system so as to be detectable, they may present signal events that are indistinguishable from relevant signal events, and would contribute to the overall signal profile from which relevant signal events must be derived.

For example, the present invention is further illustrated with reference to the monitoring of nucleic acid polymerization reactions that are used in determining the nucleotide sequences of template or target nucleic acids. In one approach, a nucleic acid sequence is determined by detecting the replication of that nucleic acid by a polymerase enzyme, which uses the underlying nucleic acid molecule as a template for the replication process. In particular, a complex of a polymerase, a template nucleic acid, and a primer nucleic acid that is complementary to a portion of the template, is provided immobilized upon a solid support, such as the surface of a transparent substrate. Nucleotide monomers bearing a detectable label, such as an optically detectable fluorescent dye, are introduced to the complex, and if complementary to the next nucleotide in the template, are incorporated by the polymerase in a primer extension reaction. By detecting when the labeled nucleotide is added, and identifying the type of nucleotide added, e.g., either by its spectrally distinct label or by virtue of having only introduced a single type of nucleotide to the complex and continuing this process along the template molecule, one can effectively read out the sequence of the underlying template. These processes have been described using a serial and iterative process whereby only a single nucleotide or a single type of nucleotide is added in the extension step, followed by washing away excess unincorporated nucleotides and detection of where the label was incorporated. See, e.g., Metzker, Nature Reviews Genetics, 11:31-46 (2010), which is hereby incorporated by reference in its entirety for all purposes and in particular for all teachings related to sequencing.

Alternative processes monitor the extension reaction in a continuous, real-time approach, where the incorporation event is detected as it occurs (rather than following a washing step). Such methods typically employ processes that allow detection of the incorporation event even in the presence of working concentrations of labeled nucleotides, by detecting a characteristic signal that is associated with the actual incorporation event. For example, as described in Eid et al., supra, the complex is provided within an optically confined region that illuminates, and thus observes, only fluorescently labeled compounds that are within a very small illumination region surrounding the complex. The result is that nucleotides that are going to be incorporated into the primer extension product are retained within the illumination volume for longer periods of time than randomly diffusing, unincorporated nucleotides. This extended presence provides a detectable signal event that is attributable to a nucleotide incorporation event. Further, by providing the detectable label on a phosphate portion of the nucleotide, the label portion is liberated during the incorporation process, thus providing an end to the signal event when the label portion diffuses out of the illumination volume.

In still other processes, the incorporation event is marked by the bringing together of interactive detectable groups, e.g., one on the nucleotide, and the other on the polymerase. When these groups are in sufficient proximity as afforded by the incorporation process, they yield a representative signal associated with the energy transfer between the groups. See, e.g., U.S. Pat. No. 7,056,676, which is hereby incorporated by reference in its entirety for all purposes and in particular for all teachings related to detection of nucleotide incorporation.

In each of the above processes, the nucleic acid polymerization complex is provided localized at or near a surface of a solid substrate. Such localization may be through immobilization of the template or primer nucleic acids to the substrate, or through immobilization of the polymerase enzyme to the substrate. Further, in each process, detection of an incorporation event is carried out by identifying a labeled nucleotide either as it is reacting with the complex, or subsequent to the reaction, when the labeled nucleotide is incorporated into the extended primer.

As will be appreciated, the presence of nonspecifically associated fluorescent label groups, either as labeled nucleotide analogs that were not incorporated, or as liberated fluorescently labeled by-products of the reaction, e.g., labeled polyphosphate groups, yields detectable signal events that are not relevant to the reaction of interest, namely nucleotide incorporation. One of the major sources of these non-specific signaling events is the adsorption of labeled groups to either the solid substrate or other immobilized components of the reaction, e.g., the polymerase enzyme. Some processes have been employed to reduce the potential for such non-specific adsorption to the underlying surface through surface passivation processes (See, e.g., U.S. Patent Application No. 2008-0176769, which is hereby incorporated by reference in its entirety for all purposes and in particular for all teachings related to passivation processes). Even with such processes, some non-specific binding can occur. For example, in some passivized surfaces, hydrophobic groups can remain on the underlying substrate surface that provides areas for non-specific adsorption of highly hydrophobic organic fluorescent labeling groups. Likewise, presence of extra charged groups may provide opportunities for association with oppositely charged detectable groups, in a non-specific fashion. Additives described herein can be used in the above-described processes to reduce and/or prevent non-specific adsorption, association or binding of certain reactants, such as labeled nucleotide analogs, to other reaction components.

The present invention is illustrated with reference to the following non-limiting examples.

EXAMPLES

Figure 2:
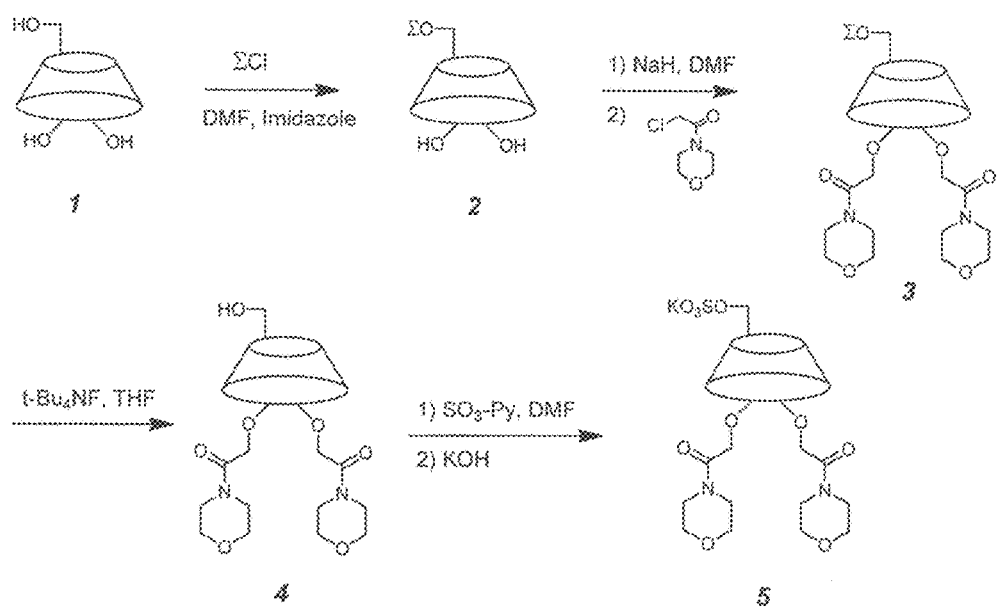
FIG. 2 shows a synthetic scheme for a substituted cyclodextrin compound, heptakis(2,3-diacetylmorpholine-6-sulfato)-β-cyclodextrin (also interchangeably referred to as SBCD-MOR, Cyclo-Mor, and cyclodextrin-morpholino).

Example 1: Synthesis of Heptakis(2,3-diacetylmorpholine-6-sulfato)-β-cyclodextrin The synthetic scheme for Compound 1 is illustrated in FIG. 2. As per the scheme shown in FIG. 2, the target compound, Heptakis(2,3-diacetylmorpholine-6-sulfato)-β-cyclodextrin, (also interchangeably referred to as SBCD-MOR, Cyclo-Mor, and cyclodextrin-morpholino) (5), was synthesized in four steps starting from anhydrous β-cyclodextrin (1). Thus, commercially available β-cyclodextrin (1) was first dehydrated in a high vacuum oven at below 100° C. to give the anhydrous material. The anhydrous 1 was then treated with TBDMSCI and imidazole in DMF to give the 6-hydroxy protected silylether 2 as shown in FIG. 2. Compound 2 was then reacted with sodium hydride and N-(chloroacetyl)morpholine in DMF under nitrogen to give the dimorpholine substituted compound 3 in good yield. Deprotection of the TBDMS group in compound 3 was achieved with (n-Bu)4NF in THF. Sulfonation of compound 4 was carried out using sulfurtrioxide pyridine complex in DMF at room temperature. After neutralizing with 6 N potassium hydroxide the crude product was dissolved in water and slowly added ethanol to it to induce the precipitation of potassium sulfate salt. The inorganic salt was then filtered off and the desired product 5 was obtained by crystallizing out from hot water and sufficient amount of ethanol.

Preparation of Anhydrous β-Cyclodextrin (1). The commercial hydrated β-cyclodextrin was placed in Pyrex brand drying trays and subjected to dehydration in an oven heated at 100° C. under high vacuum for at least 48 hours until about 14% of weight of water was removed. The anhydrous powder was then stored in a well sealed bottle.

Preparation of Heptakis(6-O-tert-butyldimethylsilyl)cyclomalto-heptaose (2). To an oven dried 2-L three-necked round bottom flask equipped with a football-shaped stir bar was added anhydrous N,N-dimethylformamide (DMF, 180 mL) under nitrogen atmosphere. The flask was heated using heating mantle and solvent was brought to near boiling. Turned off the heat and removed the flask from the mantle. Added oven dried β-cyclodextrin (89 g, 78.4 mmol) and stirred vigorously. Added imidazole (54.9 g, 806 mmol). Continued to stir vigorously until the solids were completely dissolved and the flask cooled to room temperature (total of about 30 min). A light honey-colored solution was obtained.

Slowly added dropwise a solution of tert-butyldimethylsilyl chloride (TBDMSCI, 86.86 g, 576.2 mmol) in anhydrous ethyl acetate (260 mL). The addition took approximately 3 h. The reaction was monitored with TLC (40:10:1 of CHCl3:MeOH:H2O). After stirring for 2 h additional TBDMSCI (9.09 g, 60.4 mmol) in EtOAc (26 mL) and imidazole (5.5 g) was added dropwise. Stirred for 18 h at ambient temperature. [Note: Additional TBDMSCI and imidazole may be required to consume all the undersilylated intermediates to the product. Small amount of oversilylated side-products are generally presented in the reaction mixture.

Added EtOAc (1 L) and the resultant crystals (imidazole hydrochloride) were filtered off. Rinsed with EtOAc (2×100 mL). The combined filtrate was extracted and washed with acidified water (4×100 mL). After drying over $Na_2SO_4$, the EtOAc layer was concentrated to small volume (~400 mL). The crude product was collected through filtration, washed with EtOAc/hexanes (1:2, 2×100 mL) and dried in a desiccator under high vacuum to give 131.37 g of a white solid. Redissolved the solid in hot acetone (5 L) to give an oversaturated solution. Cooled slowly to bring upon the crystallization. Filtered to collect the solid (48.3 g). Second crop of solid (52.8 g) was obtained from the filtrate and a third crop of product (~20 g) was obtained after reprocessing the second filtrate. On TLC, it revealed the first crop of product is pure and the second and the third of products showed a major spot of product and a small less-polar spot of oversilylated product.

Preparation of Heptakis(6-O-tert-butyldimethylsilyl-2,3-diacetylmorpholine)-β-cyclodextrin (3). To an oven dried 500 mL three-neck round bottom flask connected with a condenser was charged 100 mL of tetrahydrofuran (THF) under nitrogen atmosphere. To it was slowly added sodium hydride (4.456 g, 186 mmol) under nitrogen. After cease of bobbling the flask was placed in a water bath at 35° C., and a solution of 2 (11.0 g, 5.68 mmol) in THF (30 mL) and N-(chloroacetyl)morpholine (35.36 g, 216.1 mmol) was added dropwise through an addition funnel. The addition was complete in 10 min. Stirring was continued for 2 h and reaction was monitored using TLC. Added another 1 g of NaH to push the reaction to completion. The reaction took a total of 14 days. Added iodomethane (5 mL) and stirred for another 1 day. To the reaction mixture was slowly added dropwise EtOH (8 mL) in 2 min to quench the reaction. Added n-butylacetate (100 mL) and rotavapor evaporating off THF at reduced pressure until n-butylacetate starting to distill over. Added EtOAc (100 mL) and the suspension was placed in a centrifuged flask and centrifuged to separate the solid from the solvent. Filtered to collect the solid using EtOAc, washed with EtOAc (2×50 mL) and dried. The crude product was used in the next step without further purification.

Preparation of Heptakis(2,3-diacetylmorpholine)-β-cyclodextrin (4). To a solution of 3 in THF (75 mL) in a 250 mL round bottomed flask was added t-Bu4NF (75 mL, 1 M in THF) and stirred for 70 h at room temperature. TLC (40:10:1 of $CHCl_3$:MeOH:water) showed the reaction was complete. The solvent was evaporated under reduced pressure, co-evaporated with acetonitrile (2×100 mL), dried, washed with hexanes (3×100 mL) and decanted the solvent. After drying with high vacuum pump overnight there was obtained the desired product 4. The crude product was used in the next step without further purification.

Preparation of Heptakis(2,3-diacetylmorpholine-6-sulfato)-β-cyclodextrin (5). To a solution of 4 in DMF (150 mL) was added $SO_3$-pyridine complex (30.0 g, 188 mmol) and stirred for 18 hours at room temperature. LC/MS showed formation of the product peak. The solution was then poured into acetone (400 mL) and subjected to centrifugation to give the crude solid. The supernatant was decanted and the gum was dissolved in water (100 mL). Added dropwise concentrated KOH until pH=10.5. Added 300 mL of EtOH, the resultant inorganic salt was filtered off. The filtrate was concentrated to small volume (~100 mL) and to it was added hot MeOH (500 mL). After cooling to room temperature the resultant solid was collected, dried in an oven under high vacuum at 45° C. overnight to give 16.3676 g of product 5 (yield for a total of three steps from 2: 76.9%).

Example 2: Synthesis of Heptakis(2,3-diacetyldiethylacetamide-6-sulfato)-β-cyclodextrin, (SBCD-DEA)

Figure 3:
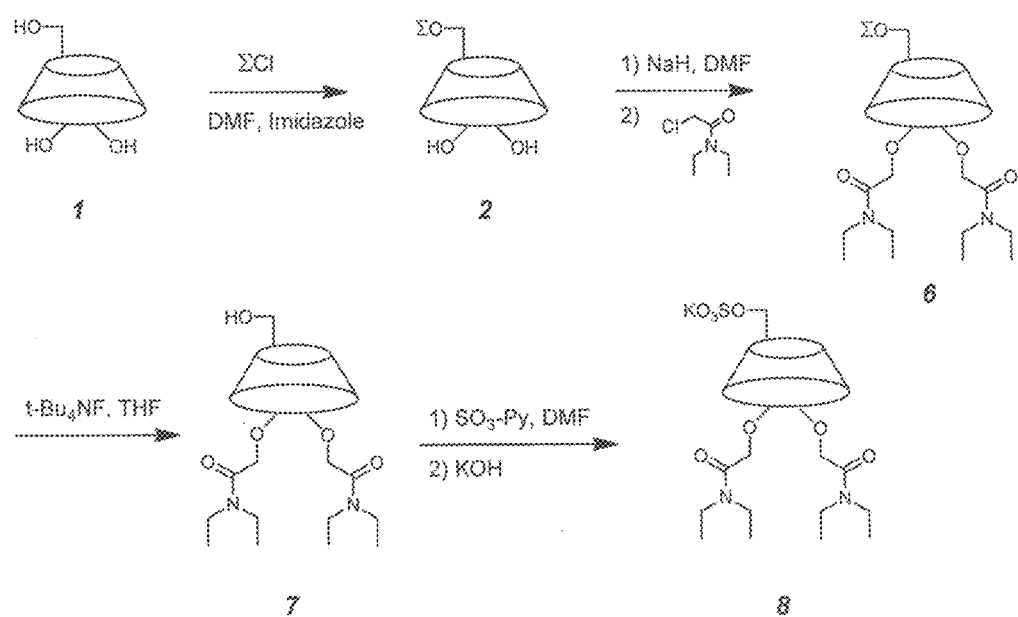
FIG. 3 shows a synthetic scheme for an alternative substituted cyclodextrin compound.

As shown in FIG. 3, the target compound, Heptakis(2,3-diacetylmorpholine-6-sulfato)-β-cyclodextrin, (SBCD-DEA) (8), was synthesized similarly in four steps starting from anhydrous β-cyclodextrin (1) as per synthesis of SBCD-MOR. Compound 2 was then reacted with sodium hydride and 2-chloro-N,N-diethylacetamide in DMF under nitrogen to give the diacetyldiethylacetamide substituted compound 6 in good yield. Deprotection of the TBDMS group in compound 6 was achieved with (n-Bu)4NF in THF. Sulfonation of compound 7 was carried out using sulfurtrioxide pyridine complex in DMF at room temperature. After neutralizing with 6 N potassium hydroxide the crude product was dissolved in water and slowly added ethanol to it to induce the precipitation of potassium sulfate salt. The inorganic salt was then filtered off and the desired product 8 was obtained by crystallizing out from hot water and sufficient amount of ethanol.

Preparation of Heptakis(6-O-tert-butyldimethylsilyl-2,3-diacetyldiethyl-acetamide)-β-cyclodextrin (6). To an oven dried 500 mL three-neck round bottom flask connected with a condenser was charged 100 mL of tetrahydrofuran (THF) under nitrogen atmosphere. To it was slowly added sodium hydride (3.134 g, 130.6 mmol) under nitrogen. After cease of bobbling the flask was placed in a water bath at 35° C., and a solution of 2 (7.00 g, 3.62 mmol) in THF (20 mL) and 2-chloro-N,N-diethylacetamide (20 mL, 145.6 mmol) was added dropwise through an addition funnel. The addition was complete in 10 min. Stirring was continued for 2 h and reaction was monitored using TLC. Added another 1 g of NaH to push the reaction to completion. The reaction took a total of 14 days. Added iodomethane (5 mL) and stirred for another 1 day. To the reaction mixture was slowly added dropwise EtOH (8 mL) in 2 min to quench the reaction. Added n-butylacetate (100 mL) and rotavapor evaporating off THF at reduced pressure until n-butylacetate starting to distill over. Added EtOAc (100 mL) and the suspension was placed in a centrifuged flask and centrifuged to separate the solid from the solvent. Filtered to collect the solid using EtOAc, washed with EtOAc (2×50 mL) and dried. The crude product was used in the next step without further purification.

Preparation of Heptakis(2,3-diacetyldiethylacetamide)-β-cyclodextrin (7). To a solution of 6 in THF (60 mL) in a 250 mL round bottomed flask was added t-Bu4NF (75 mL, 1 M in THF) and stirred for 70 h at room temperature. TLC (40:10:1 of CHCl3:MeOH:water) showed the reaction was complete. The solvent was evaporated under reduced pressure, co-evaporated with acetonitrile (2×100 mL), dried, washed with hexanes (3×100 mL) and decanted the solvent. After drying with high vacuum pump overnight there was obtained the desired product 6. The crude product was used in the next step without further purification.

Preparation of Heptakis(2,3-diacetyldiethylacetamide-6-sulfato)-β-cyclodextrin (8). To a solution of 7 in DMF (120 mL) was added $SO_3$-pyridine complex (30.0 g, 188 mmol) and stirred for 18 h at room temperature. LC/MS showed formation of the product peak. The solution was then poured into acetone (400 mL) and subjected to centrifugation to give the crude solid. The supernatant was decanted and the gum was dissolved in water (100 mL). Added dropwise concentrated KOH until pH=10.5. Added 300 mL of EtOH, the resultant inorganic salt was filtered off. The filtrate was concentrated to small volume (~100 mL) and to it was added hot MeOH (500 mL). After cooling to room temperature the resultant solid was collected, dried in an oven under high vacuum at 45° C. overnight to give 10.1083 g of product 8 (yield for a total of three steps from 2: 78.8%).

Example 3: Single Molecule, Real-Time DNA Sequencing with Sulfated Cyclodextrins Single molecule, real-time DNA sequencing was carried out using a Pacific Biosciences® SMRT® Sequencing platform, see, e.g., Eid et al., Science Vol. 323 no. 5910 pp. 133-138 (January 2009), where individual polymerase/template/primer complexes are disposed within the observation volume of zero mode waveguides in ZMW arrays. The reaction observes, in real time, the reaction of the complexes with nucleoside polyphosphates that include detectable fluorescent labeling groups. Because these groups are labeled on the phosphate chain, the label groups are not incorporated into the primer extension product, and only the transient interaction of the complex with the labeled portion of the nucleotide is detected.

Four color, single molecule real time DNA sequencing reactions were carried out using a standard SMRT sequencing protocols and reagents on a Pacific Biosciences SMRT® Sequencing prototype system. Reactions were carried out in the presence and absence of heptakis(2,3-diacetylmorpholine-6-sulfato)-β-cyclodextrin at 120 µM.

Figure 4:
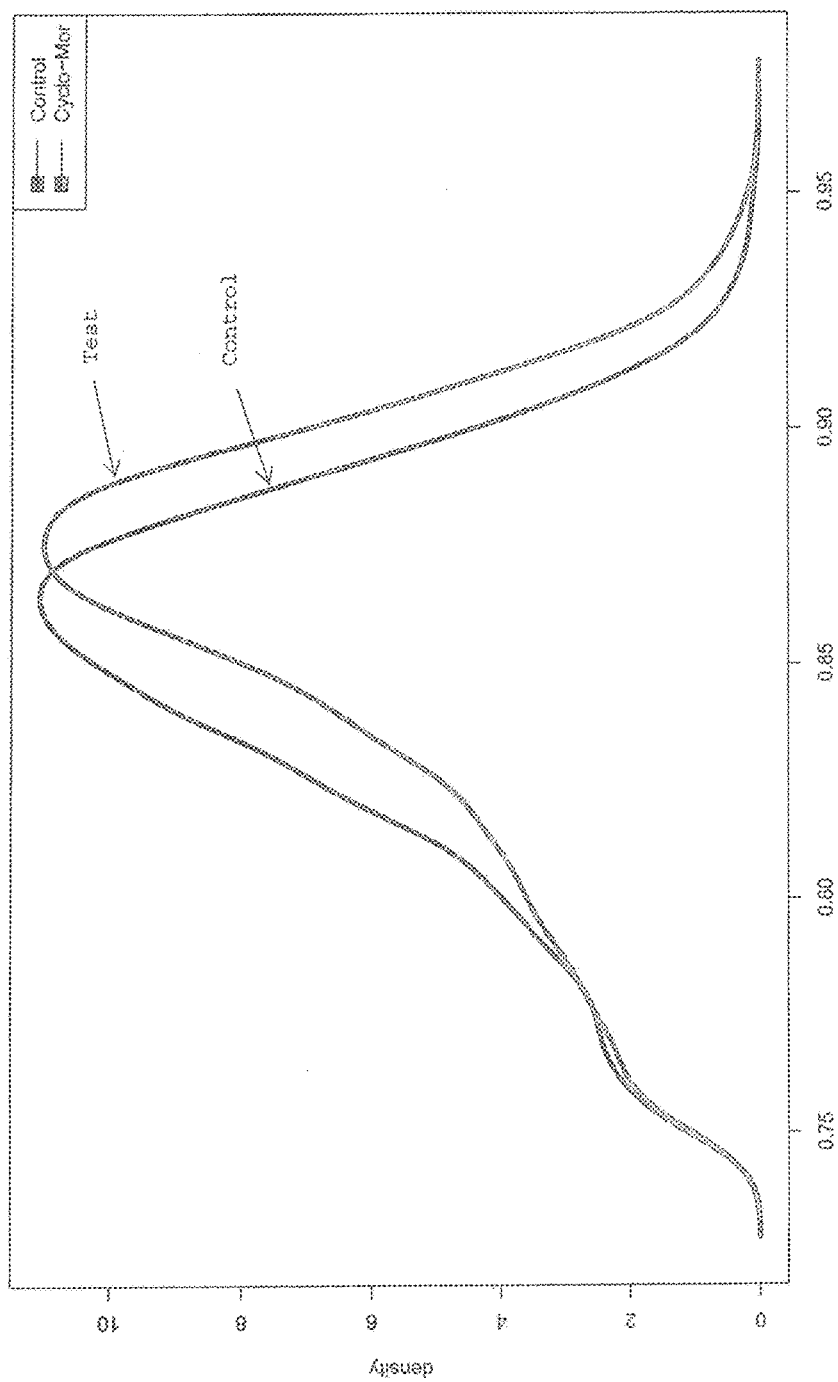
FIG. 4 shows a comparison of raw sequence read accuracy in the absence and presence of substituted cyclodextrin compounds ("Cyclo-Mor" refers to cyclodextrin-morpholino or heptakis(2,3-diacetylmorpholine-6-sulfato)-β-cyclodextrin).

FIG. 4 illustrates increased raw sequence read accuracy (percentage of bases from the template that were accurately identified within a single sequencing pass) from the test sequencing reaction that includes the cyclodextrin compound. As can be seen, the overall accuracy of the system is increased in the presence of the cyclodextrin compounds by approximately 1 percentage point over the control. Without being bound to any particular theory of operation, it is believed that the non-specific surface or other adsorption of labeled reagents to the substrate surface or the molecular complex increases error rate and thus decreases the measured accuracy, which the cyclodextrin compounds serve to mitigate.

Figure 5:
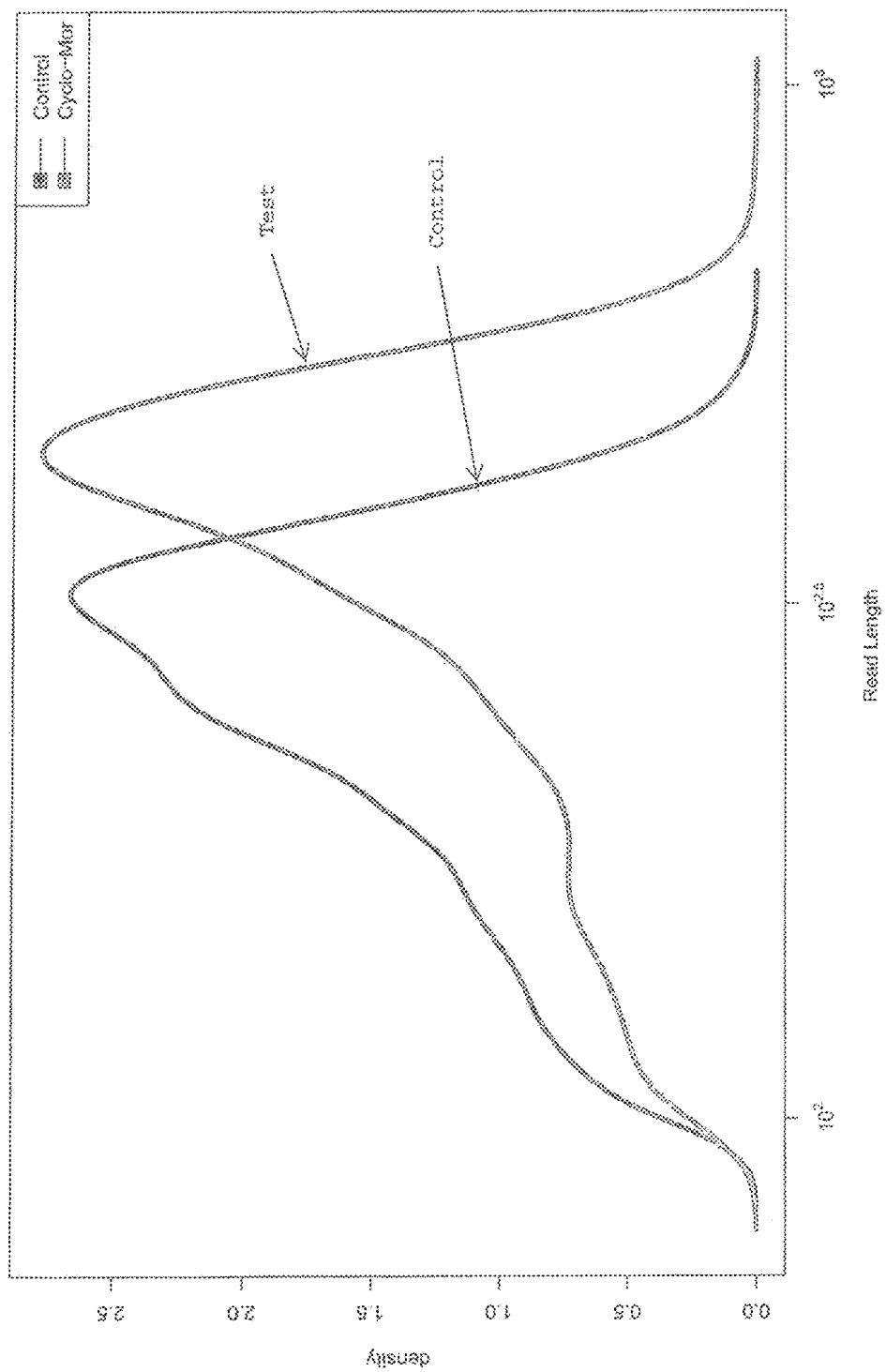
FIG. 5 shows a comparison of average readlengths for determined sequences in the absence and presence of substituted cyclodextrin compounds ("Cyclo-Mor" refers to cyclodextrin-morpholino or heptakis(2,3-diacetylmorpholine-6-sulfato)-β-cyclodextrin).

FIG. 5 shows a comparison of average read lengths obtained from sequencing reactions in the presence and absence of the cyclodextrin compound. As can be seen, the test reaction demonstrates a marked increase in mapped readlength (number of identified bases in a contiguous sequence from a single zero mode waveguide/reaction complex) for the template sequence used by 30%, or a total average readlength increase of approximately 170 bases. Accordingly, the addition of the cyclodextrin compounds provided marked improvements in at least two important reaction quality metrics of readlength and accuracy.

Example 4: Screening Sulfonated Cholic Acids

In certain aspects, sulfonated cholic acids have similar effects to cyclodextrin compounds. Taurocholic acid ($1\times SO_3^-$) and a mixture of 2×, 3×, and 4× sulfonated cholic acids were both tested.

Four-color sequencing with standard FCR chemistries was conducted under the following conditions: 120 µM Cyclodextrin control, No additive negative control, 120 µM SY427-31 (single $SO_3^-$, 480 µM SY427-31, 120 µM SY427-29 (mixture), 480 µM SY427-29. (See FIG. 6 for an illustration of the compounds used).

Both cholic acid solutions acted similarly to cyclodextrin in their ability to reduce IPDs for FRET-labeled nucleotide analogs. Without being bound by theory, one possible mechanism of the effect of these compounds is by blocking analog binding sites. It appeared that SY427-29 (mixture) required a higher concentration while SY427-31 (single $SO_3^-$ was effective at lower concentrations.

While the foregoing invention has been described in some detail for purposes of clarity and understanding, it will be clear to one skilled in the art from a reading of this disclosure that various changes in form and detail can be made without departing from the true scope of the invention. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. A reaction mixture comprising:
   a first reaction component coupled to a surface of a solid support, wherein said first reaction component comprises a polymerase;
   a second reaction component having a detectable property;
   a first additive that reduces interpulse duration (IPD), wherein said first additive comprises a member selected from cholesterol, a cholic acid derivative, poly dT oligonucleotides, cyclodextrin, and a cyclodextrin derivative;
   a second additive that reduces non-specific interactions between said first reaction component and a surface upon which said reaction mixture is disposed, wherein said second additive comprises a member selected from an organic solvent, dimethylformamide (DMF), a detergent, and N-formylmorpholine (FMP); and
   a third additive that reduces polymerase pausing, wherein said third additive comprises an aromatic ring and two —$NR_2$ substituents.

2. The reaction mixture of claim 1, wherein said cholic acid derivative is taurocholic acid.

3. The reaction mixture of claim 1, wherein said second additive is DMF.

4. The reaction mixture of claim 1, wherein said second additive is FMP.

5. The reaction mixture of claim 1, wherein said cyclodextrin derivative is a sulfated cyclodextrin having the structure:

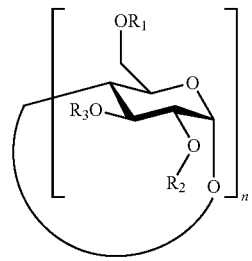

wherein n is from 6 to 12;
$R_1$ is a group that is non-attractive to the second reaction component;

R₂ and R₃ are associative groups to the surface of said solid support;
said sulfated cyclodextrin being present at an isomeric purity of at least 80%.

6. The reaction mixture of claim 5, wherein R1 is a sulfate group.

7. The reaction mixture of claim 5, wherein R2 and R3 are selected from alkyl, acetamide, hydroxyalkyl, acyl, aryl, or heteroaryl groups.

8. The reaction mixture of claim 7, wherein R2 and R3 are selected from CH2-acyl, diethylacetamide, dipropylacetamide, morpholino, piperazine, piperidine, pyrrolidine, and oxazolidine.

9. The reaction mixture of claim 1, wherein said surface comprises a plurality of first reaction components, and wherein said plurality of first reaction components are provided disposed on said surface as single molecules or single molecular complexes, each of which is resolvable from others of said first reaction components disposed on said surface.

10. The reaction mixture of claim 9, wherein said plurality of first reaction components are disposed within the observation volume of zero mode waveguides.

11. The reaction mixture of claim 1, wherein said solid support comprises a silica based substrate.

12. The reaction mixture of claim 1, wherein said second reaction component comprises a fluorescent labeling moiety.

13. The reaction mixture of claim 1, wherein said second reaction component comprises a nucleotide analog.

14. The reaction mixture of claim 1, wherein said organic solvent is dimethyl sulfoxide (DMSO) or dimethylacetamide (DMA).

15. The reaction mixture of claim 1, wherein said third additive comprising an aromatic ring and two —NR2 substituents is N,N-dimethyl-m-phenylenediamine (DMMP) or N,N-dimethyl-p-phenylenediamine (DMPP).

16. The reaction mixture of claim 1, further comprising an additive for photodamage mitigation.

17. The reaction mixture of claim 16, wherein said additive for photodamage mitigation is selected from the group consisting of a triplet state quencher, an oxygen scrubber, dithiothreitol (DTT), and mercaptoethylamine (MEA).

* * * * *